(12) United States Patent
Fuchs et al.

(10) Patent No.: US 7,084,183 B2
(45) Date of Patent: Aug. 1, 2006

(54) DIFUNCTIONAL PHOTOINITIATORS

(75) Inventors: André Fuchs, Schliengen-Obereggenen (DE); Rinaldo Hüsler, Basel (CH); Christian Schregenberger, Olsberg (CH); Martin Kunz, Efringen-Kirchen (DE)

(73) Assignee: Ciba Specialty Chemcials Corp., Tarrytown, NY (US)

( * ) Notice: Subject to any disclaimer, the term of this patent is extended or adjusted under 35 U.S.C. 154(b) by 85 days.

(21) Appl. No.: 10/494,593

(22) PCT Filed: Oct. 31, 2002

(86) PCT No.: PCT/EP02/12160

§ 371 (c)(1),
(2), (4) Date: May 5, 2004

(87) PCT Pub. No.: WO03/040076

PCT Pub. Date: May 15, 2003

(65) Prior Publication Data

US 2005/0004249 A1   Jan. 6, 2005

(30) Foreign Application Priority Data

Nov. 8, 2001   (EP)   ................... 01811020

(51) Int. Cl.
*C08F 2/50* (2006.01)
*C07C 49/83* (2006.01)
*C07C 45/64* (2006.01)
*C07C 45/81* (2006.01)
*G03F 7/031* (2006.01)

(52) U.S. Cl. ............... 522/36; 522/42; 522/114; 522/103; 568/397; 568/410; 568/336

(58) Field of Classification Search ........ 522/36, 522/42; 568/336, 397
See application file for complete search history.

(56) References Cited

U.S. PATENT DOCUMENTS

| 4,308,400 | A | | 12/1981 | Felder et al. ............... 568/336 |
| 4,721,734 | A | * | 1/1988 | Gehlhaus et al. ............... 522/8 |
| 4,987,159 | A | | 1/1991 | Li Bassi et al. ............... 522/36 |
| 5,942,290 | A | | 8/1999 | Leppard et al. ............... 427/510 |

FOREIGN PATENT DOCUMENTS

| EP | 0003002 | 7/1979 |
| WO | 2004/009651 | 1/2004 |

* cited by examiner

*Primary Examiner*—Susan Berman
(74) *Attorney, Agent, or Firm*—Tyler A. Stevenson

(57) ABSTRACT

The invention relates to α-hydroxy ketones of formula I or IIa; or mixtures of compounds of formula I and II; or mixtures of compounds of formulae Ia and IIa

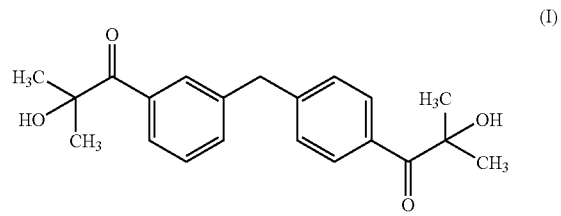

(I)

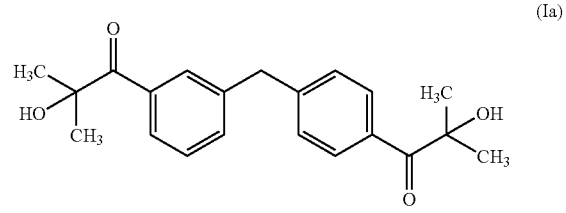

(Ia)

solvent

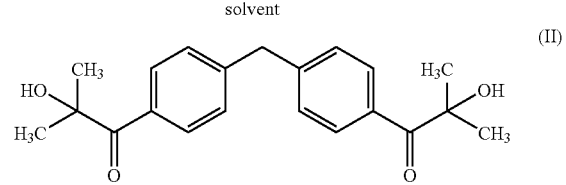

(II)

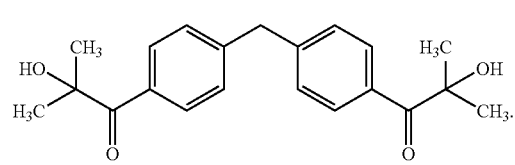

(IIa)

solvent

11 Claims, 14 Drawing Sheets

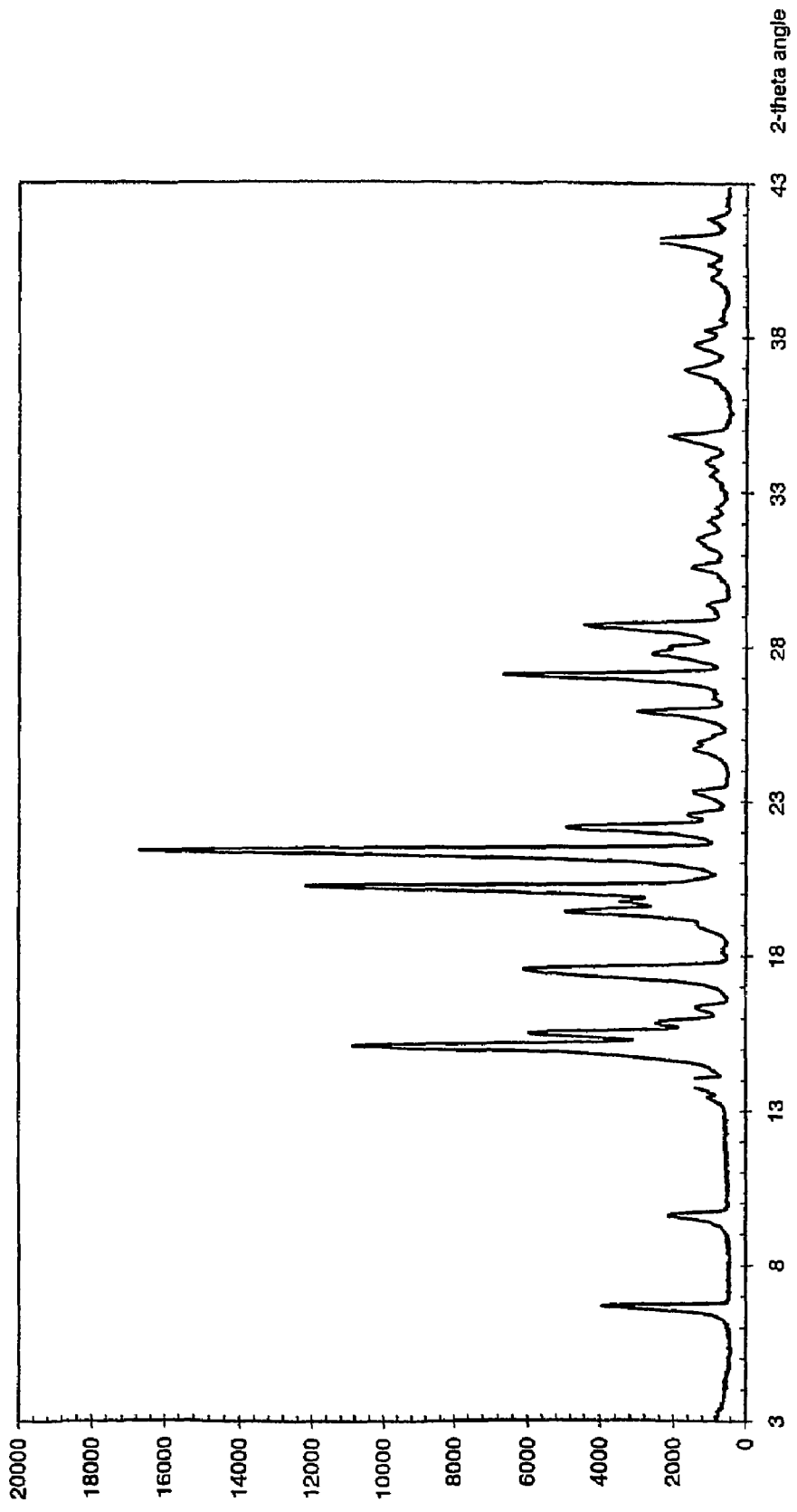

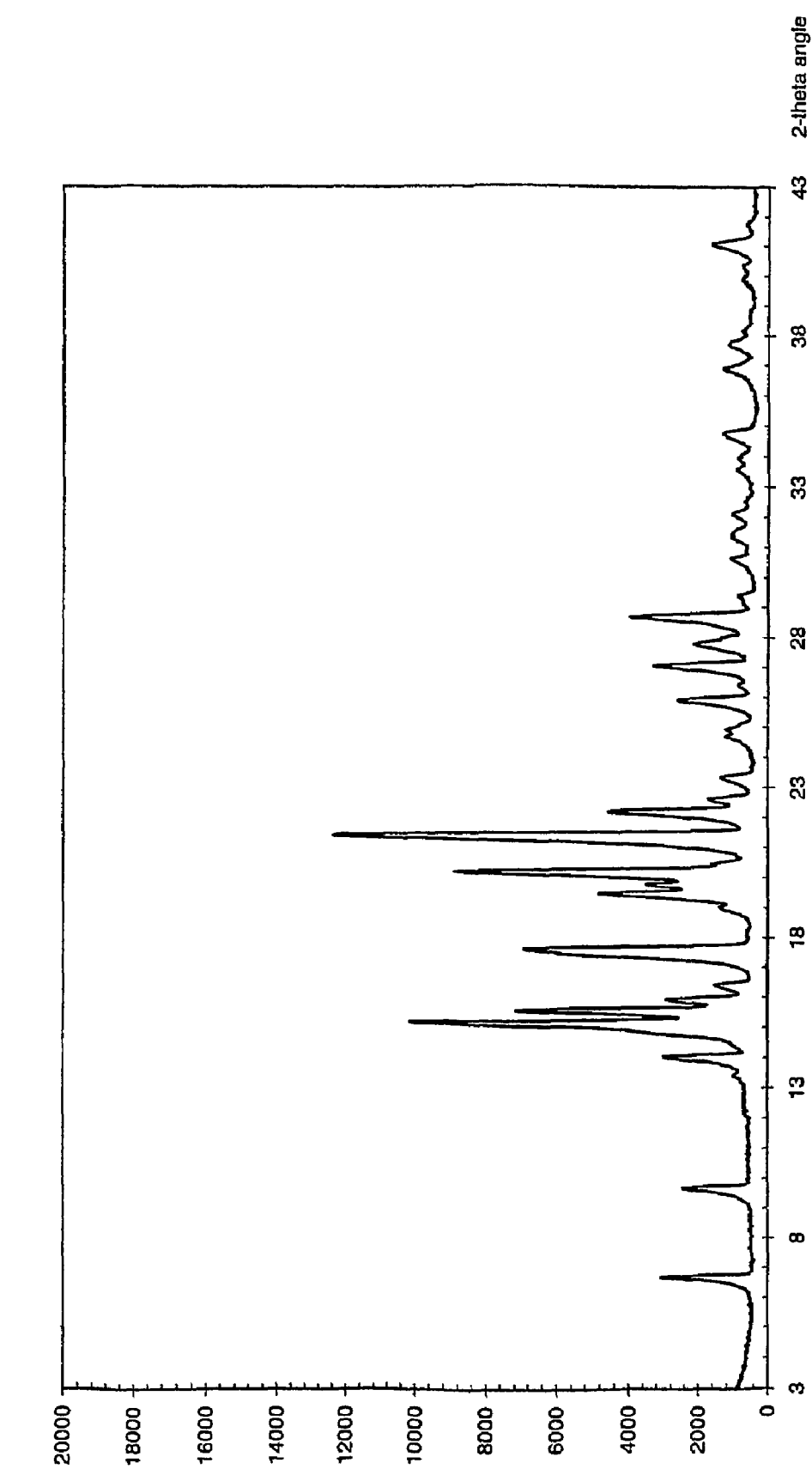
Fig. 2 Example 1.3b

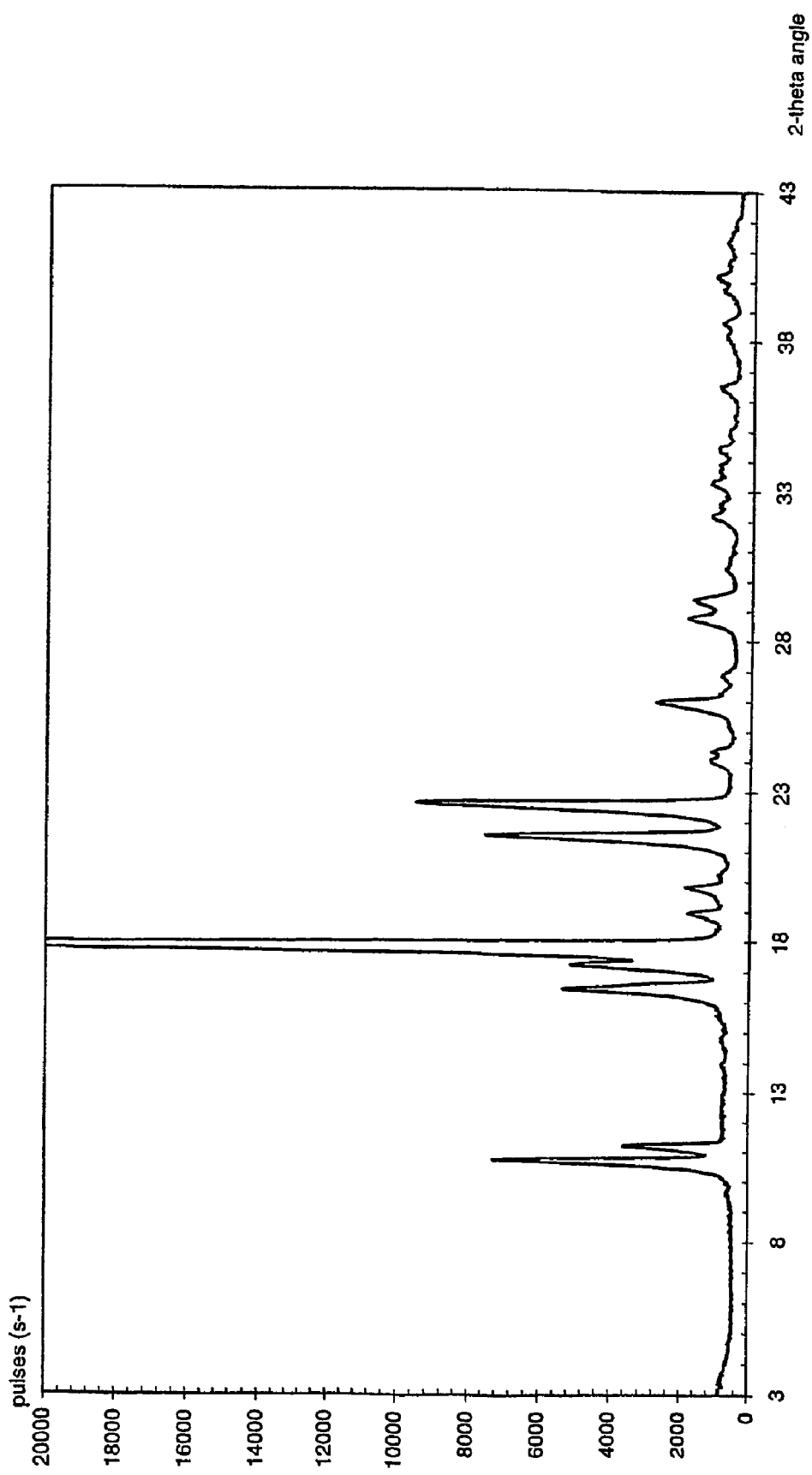
Fig. 3 Example 2

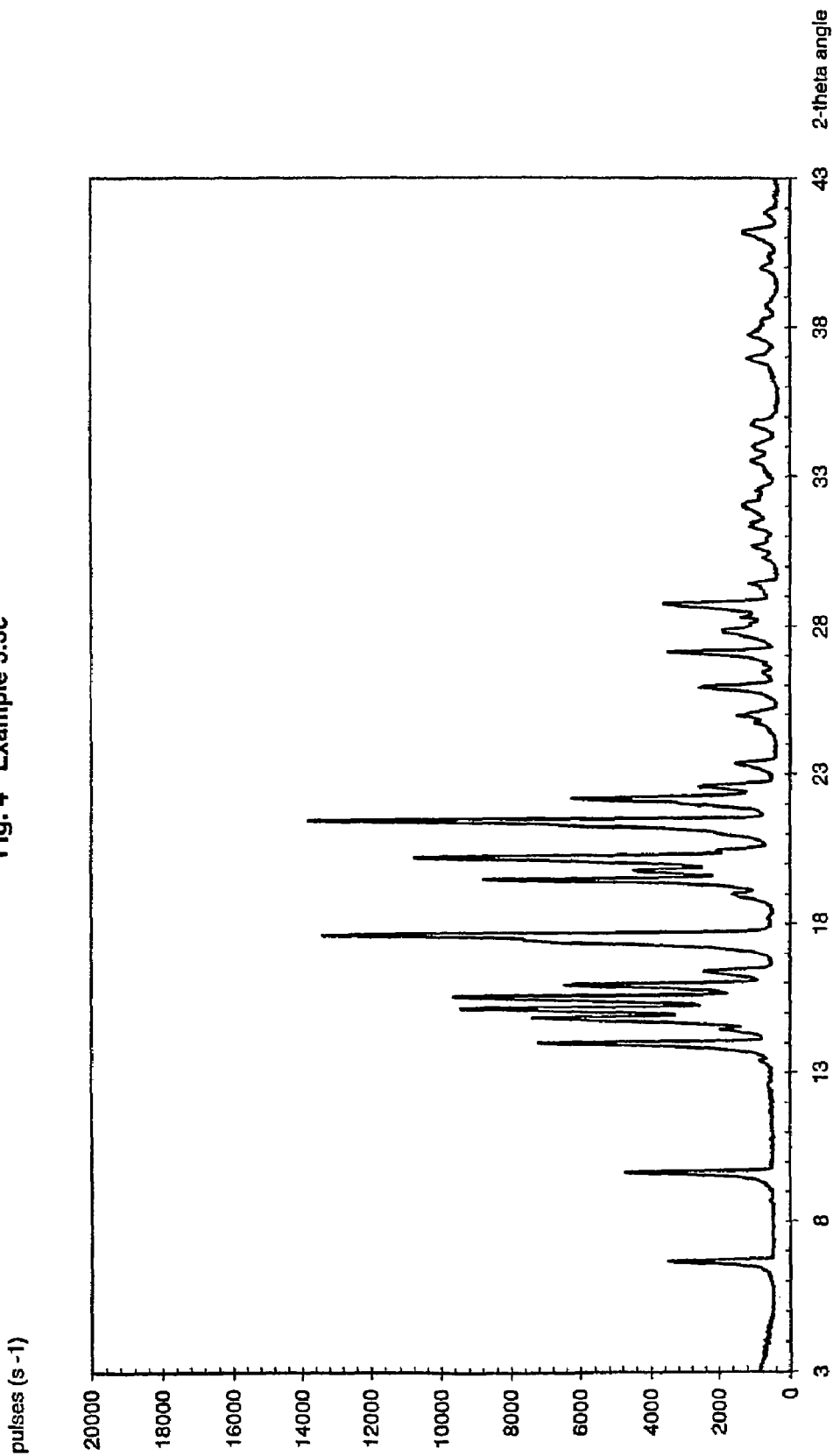
Fig. 4 Example 3.3c

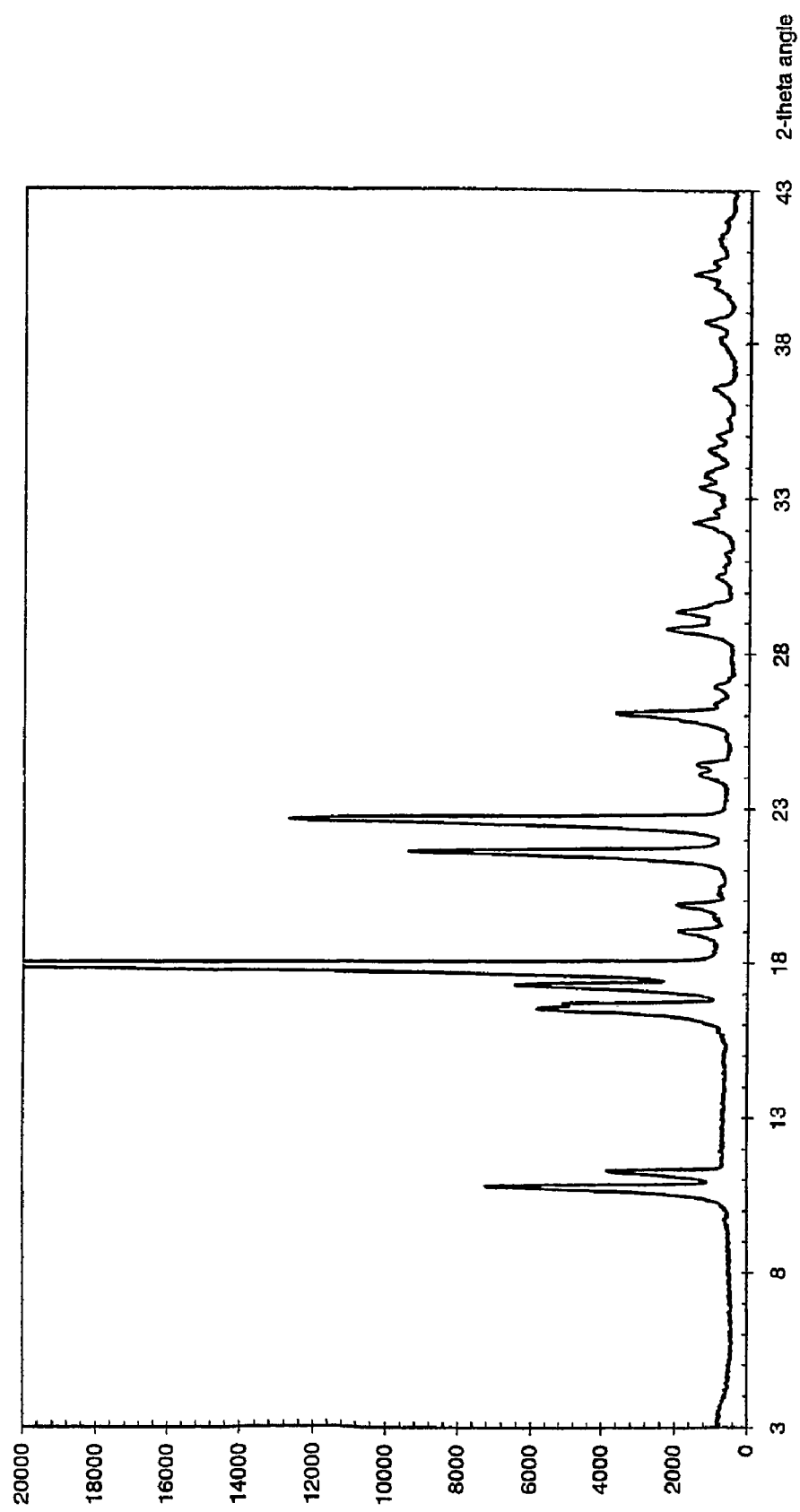
Fig. 5 Example 7

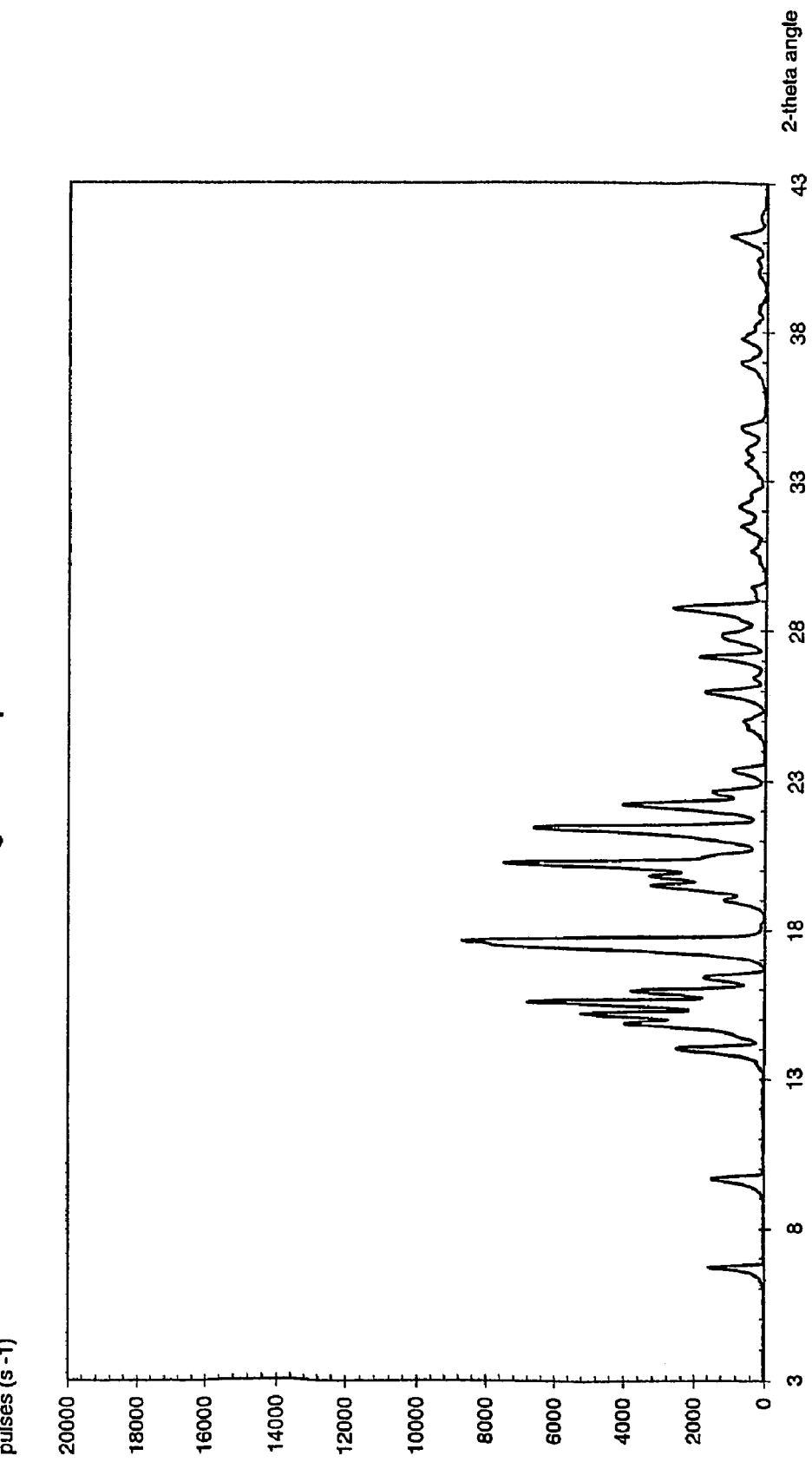

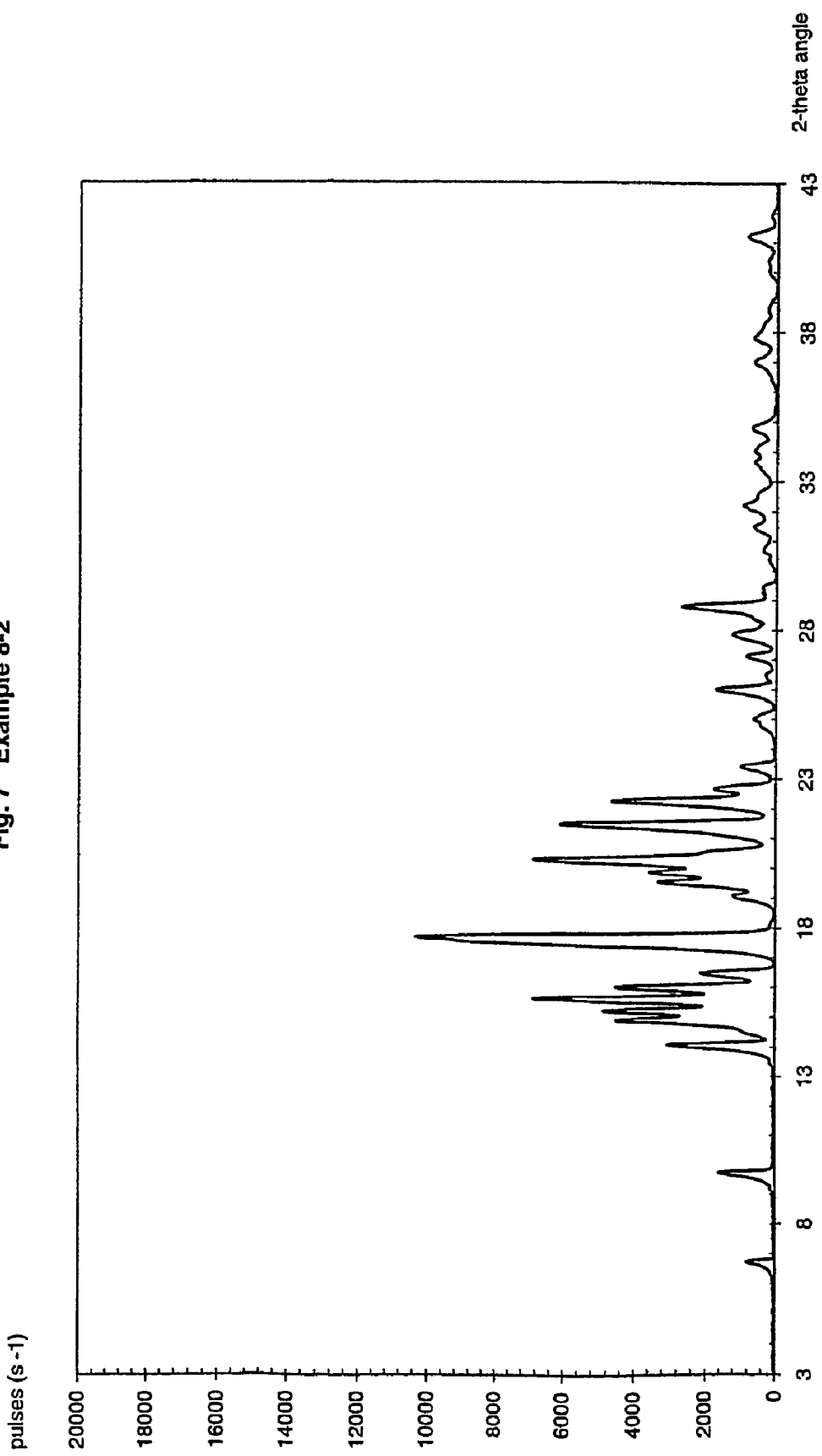

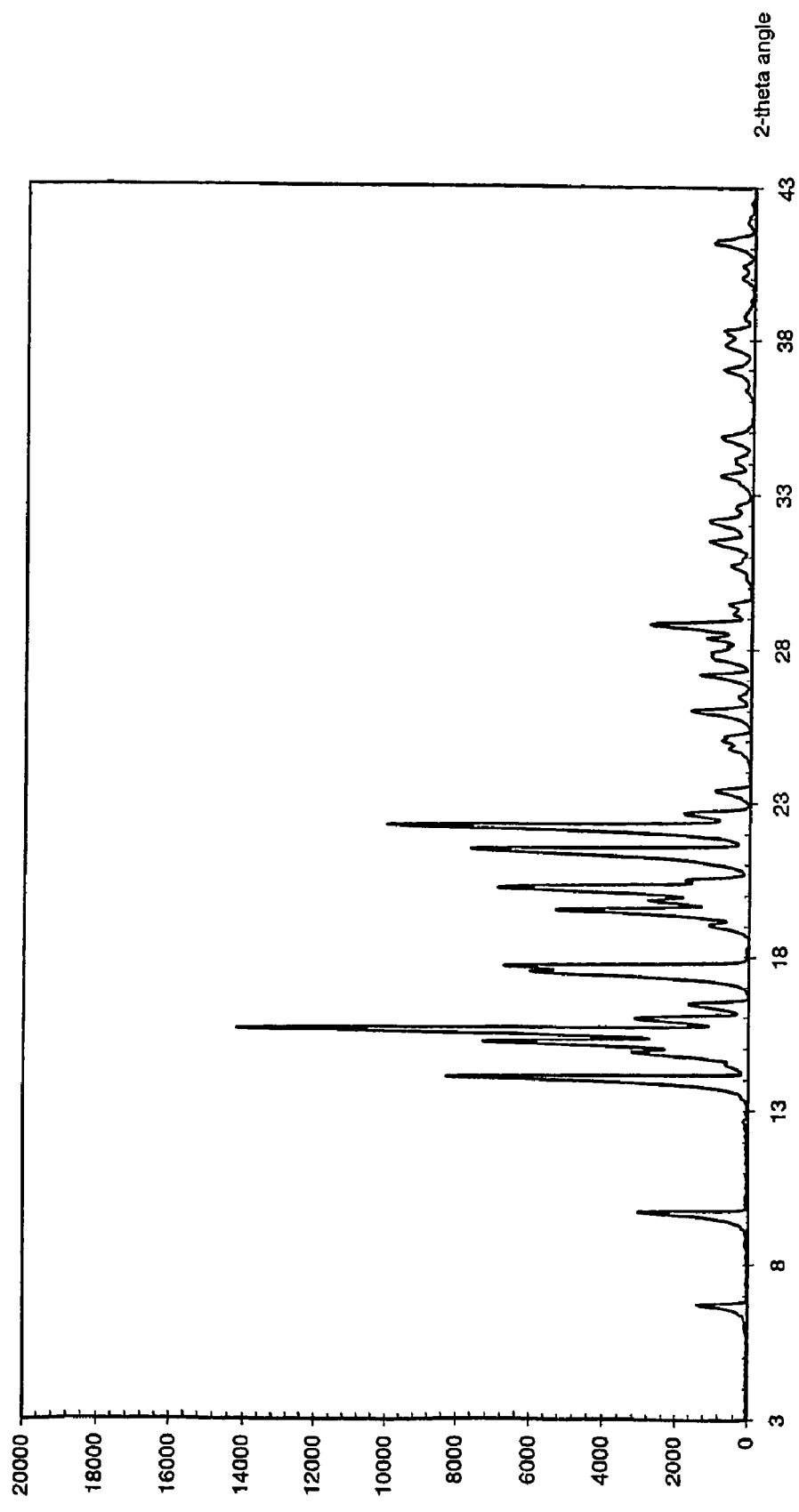
Fig. 8 Example 8-3.3c

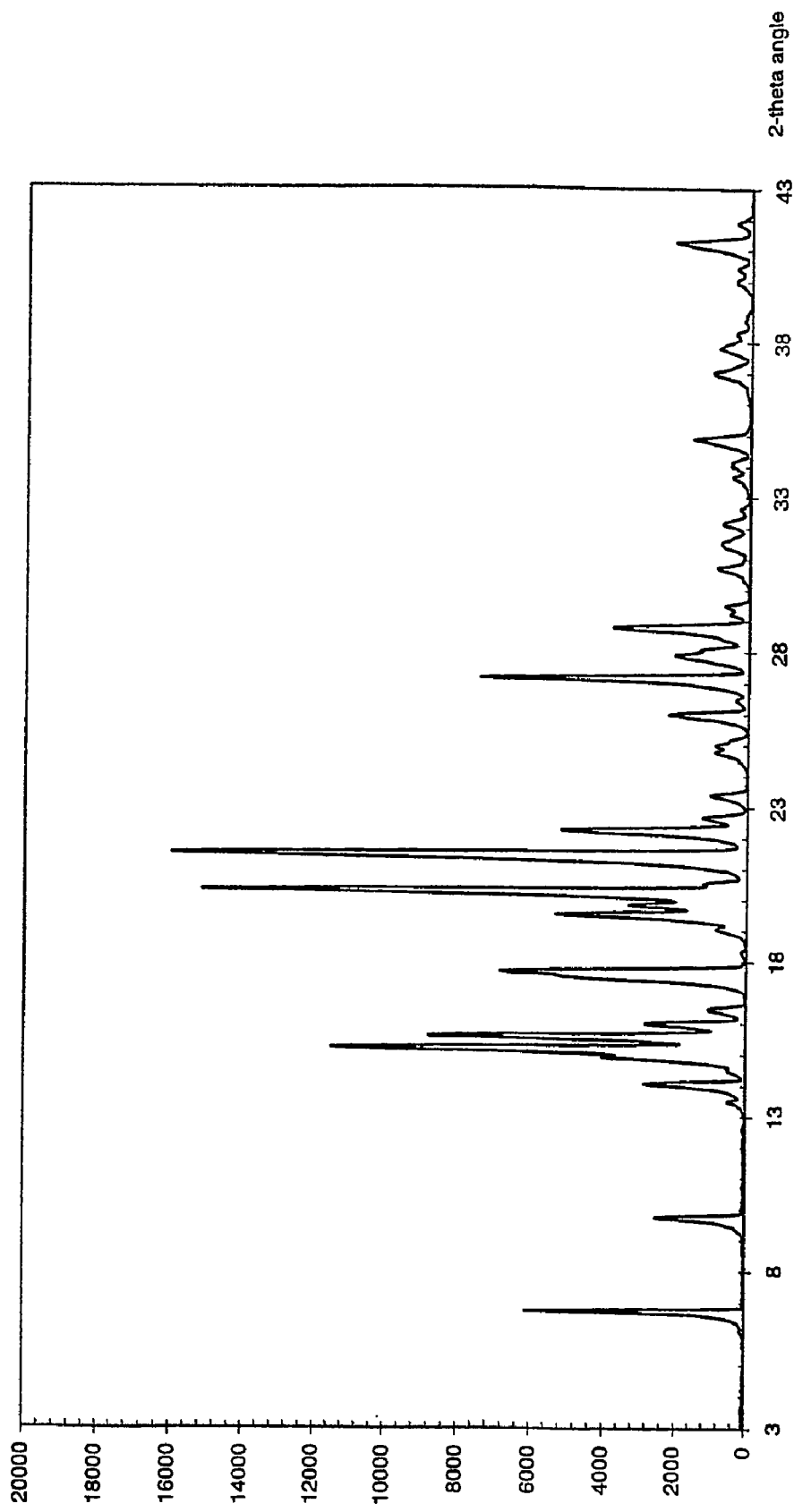
Fig. 9 Example 8-5a

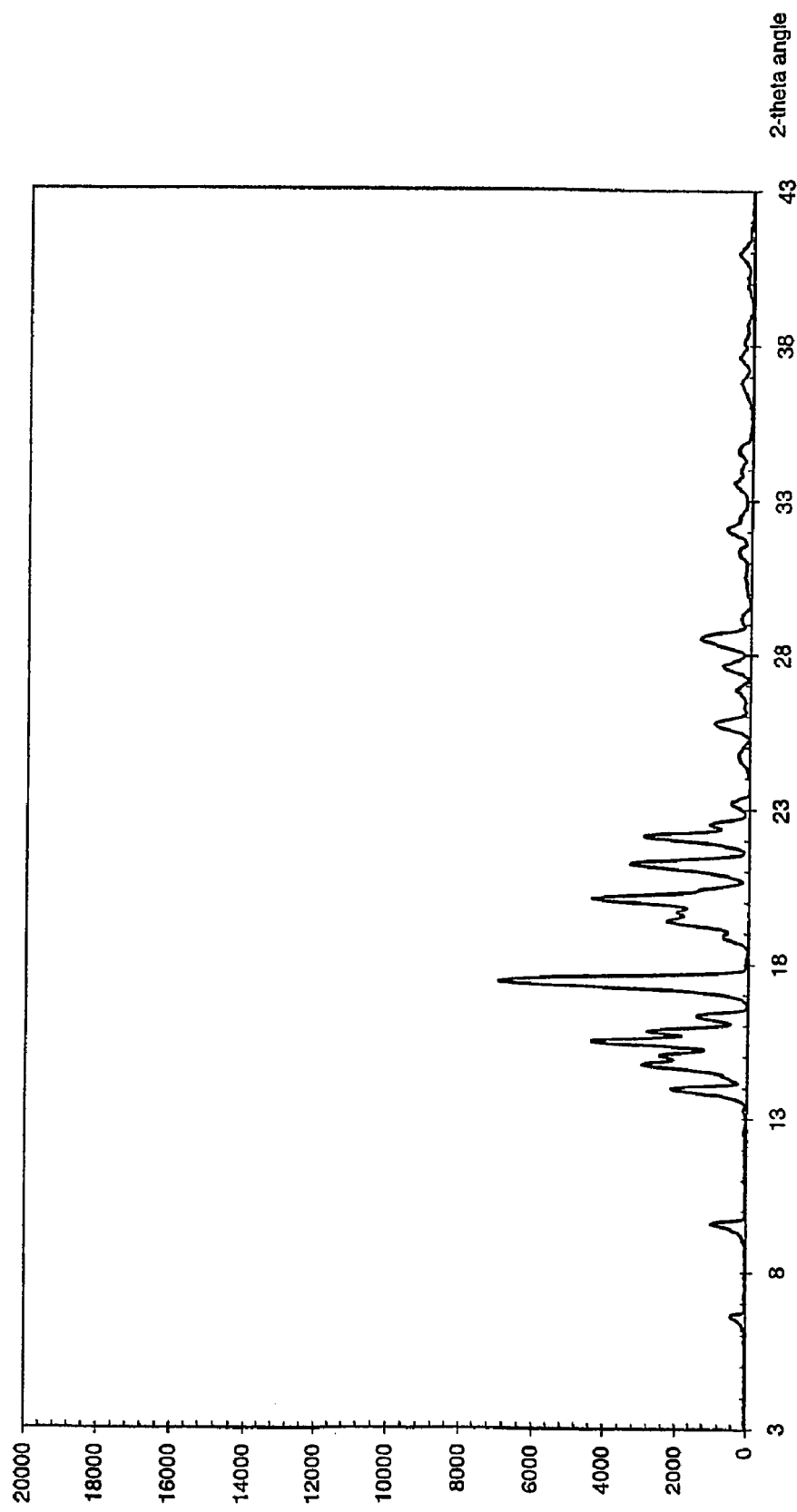
Fig. 10 Example 8-6a

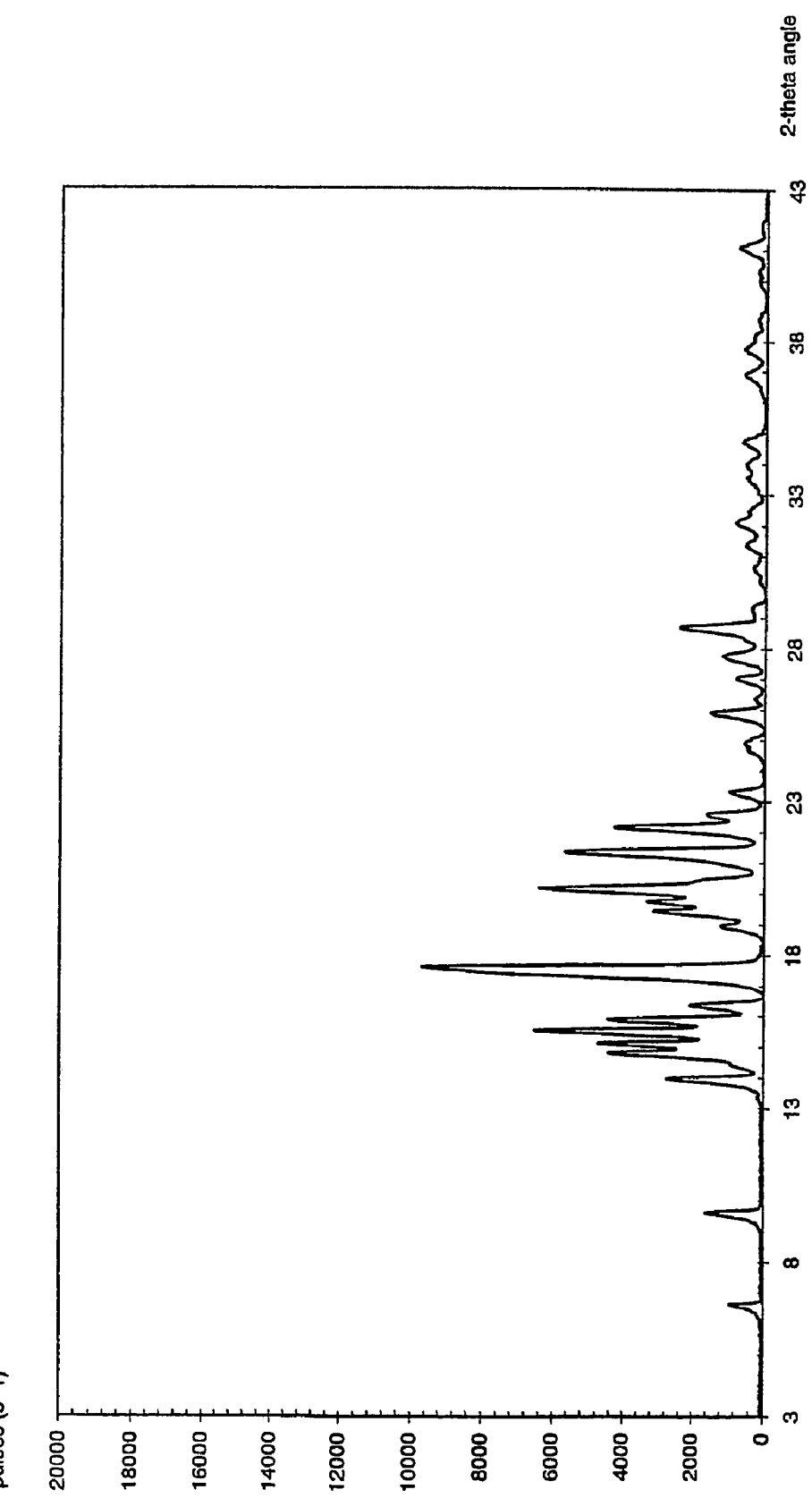

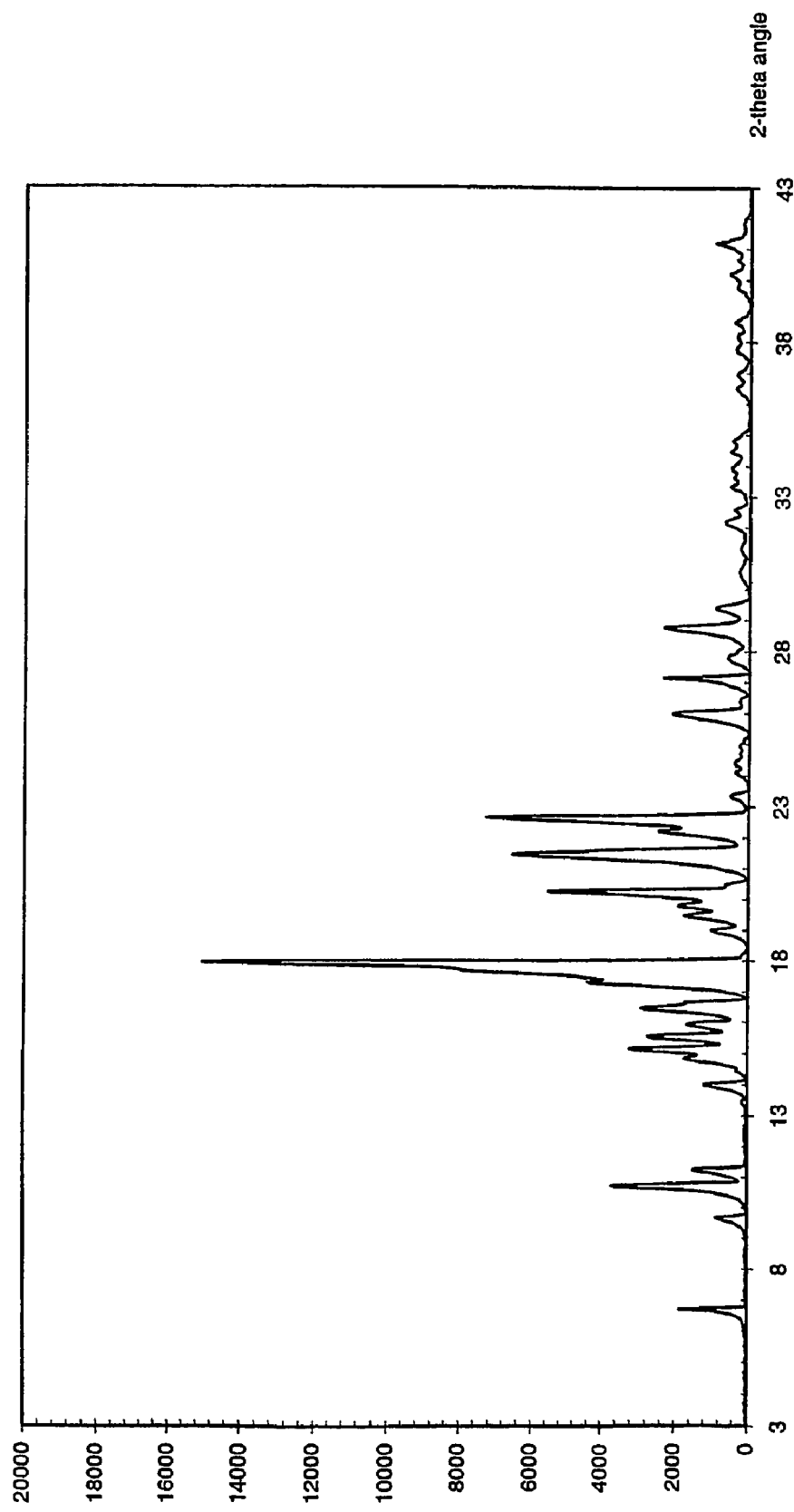
Fig. 12 Example 8-1.3c dried

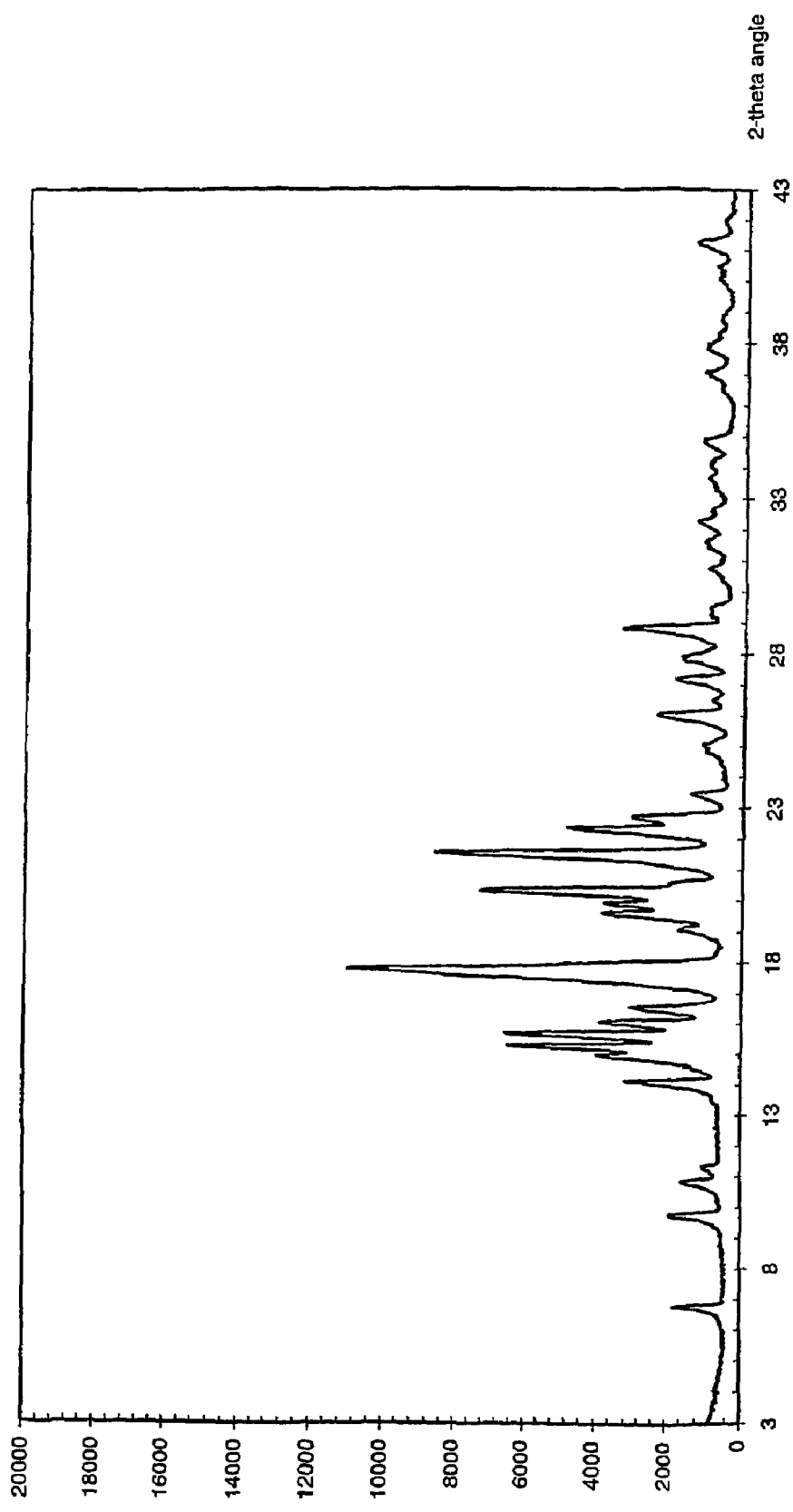

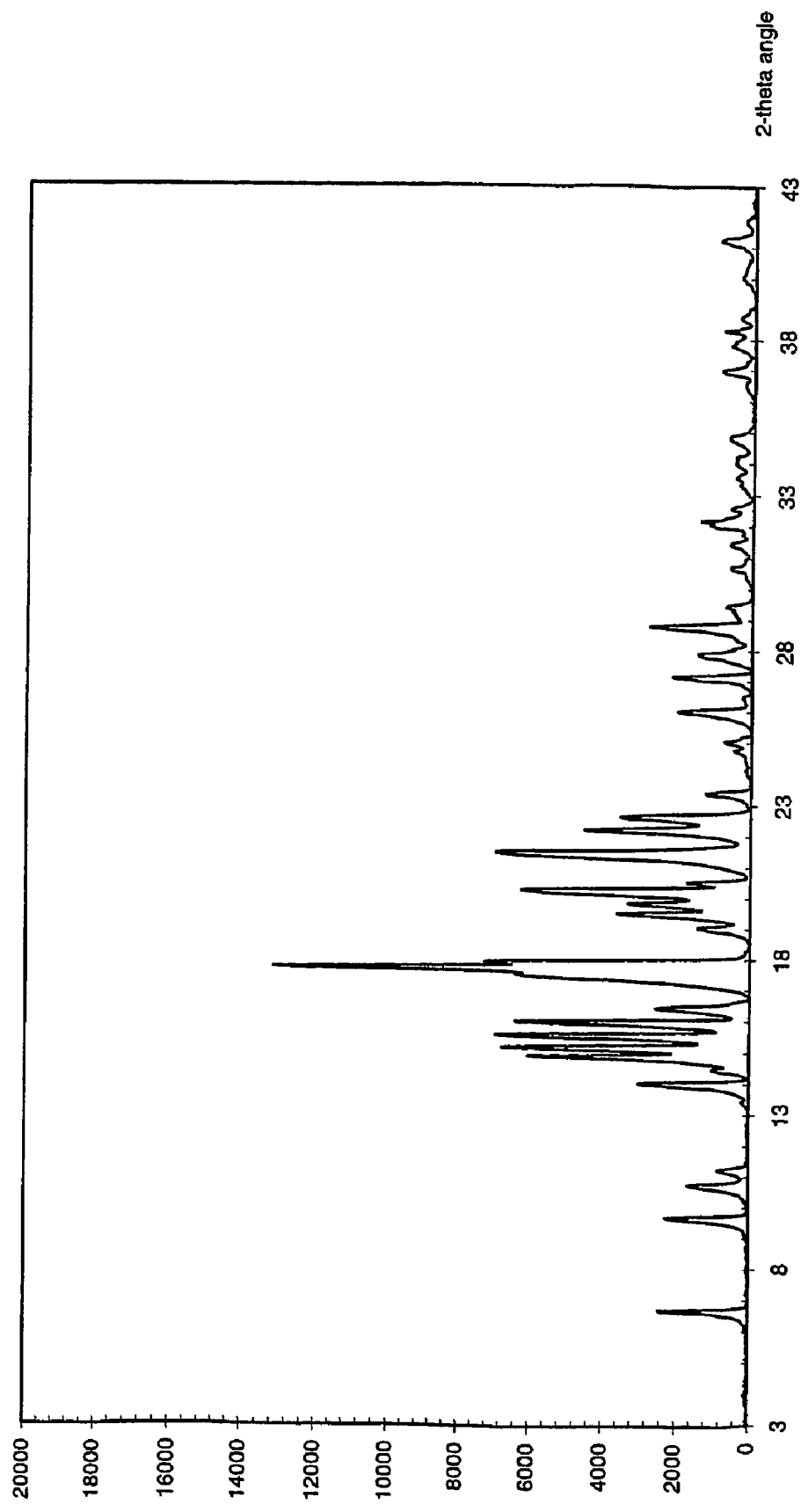
Fig. 14 Example 8-3.3c dried

DIFUNCTIONAL PHOTOINITIATORS

The invention relates to initiators and mixtures thereof for compositions that cure by means of radiation, especially using ultraviolet and visible radiation, to intermediates for their preparation, and to a process for the preparation of the initiators from the intermediates.

Systems that cure by means of radiation can be used in a large number of applications, for example in overprint coatings, printing inks, in the manufacture of electronic printed circuit boards and printing plates, and in the coating of various substrates, such as wood, plastics, paper, glass or metal. For the efficient polymerisation of such systems, it is necessary to use a photoinitiator, from which, as a result of interaction with electromagnetic radiation, reactive particles such as free radicals or cations (protons) are generated. A disadvantage of most of the initiators frequently used in practice is the undesirable odour that is produced when they are used. There is therefore a demand in the art for low-odour, low-volatility photoinitiators. In addition, it is desirable for the photoinitiator to contribute towards an improved crosslinking density and to produce fewer photolysis products capable of migration. Moreover, the photoinitiator should be available in a form which is easy to handle, should cause minimal yellowing of the cured film, and should be readily soluble in systems that cure by means of radiation.

A further important criterion for the use of photoinitiators is the effectiveness with which the reactive constituents of the formulation are polymerised. This has a direct effect on the curing rate which can be achieved during use, and on the degree of crosslinking of the resulting polymer.

European Patent Application EP-A 003 002 describes the use of particular ketones as photoinitiators. The ketones have a tertiary alpha carbon atom which is substituted by a hydroxyl group or an amino group or an etherification or silylation product thereof. The compound 4,4'-bis(α-hydroxy-isobutyryl)-diphenylmethane is listed by way of example, but its preparation is not described and characteristic properties of the compound are not mentioned. European Patent Application EP-A 003 002 also makes no reference to α-hydroxy ketones that contain water of crystallisation.

The most frequently used α-hydroxy ketone is Darocur 1173® (2-hydroxy-2-methyl-1-phenylpropan-1-one), a liquid photoinitiator which is available commercially (from Ciba Specialty Chemicals).

It has now been found that α-hydroxy ketones of the following formulae possess the required properties as photoinitiators.

The invention accordingly relates to novel crystalline and liquid α-hydroxy ketones of formula I or IIa

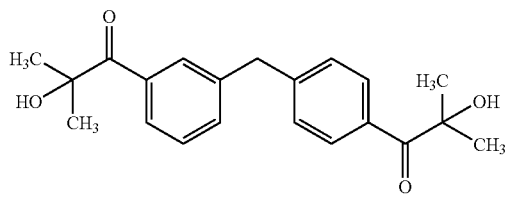

I

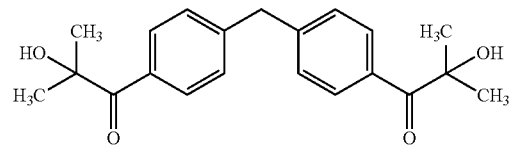

IIa solvent or mixtures of compounds of formulae I and II

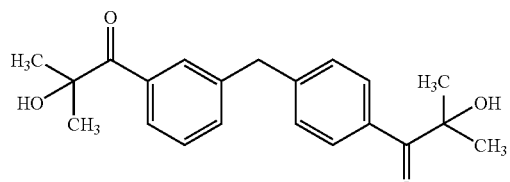

I

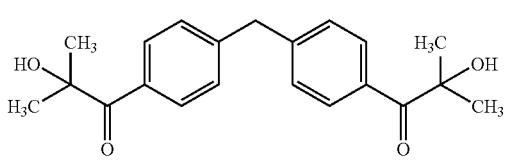

II or mixtures of compounds of formulae Ia and IIa

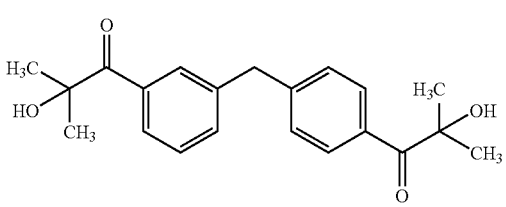

Ia solvent

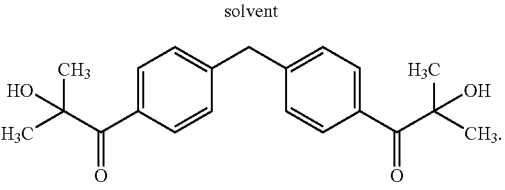

IIa solvent

The compounds and mixtures having the formulae II and IIa are crystalline and may be characterised by X-ray powder spectra according to FIGS. 1 to 5.

FIGS. 1 and 2 show the X-ray powder spectra of water-containing isomeric mixtures of the compounds of formulae Ia and IIa.

FIG. 3 shows the X-ray powder spectrum of the water-free isomeric mixture of the compounds of formulae I and II.

FIG. 4 shows the X-ray powder spectrum of the water-containing pure para-para compound of formula IIa.

FIG. 5 shows the X-ray powder spectrum of the water-free pure para-para compound of formula II.

For the preparation of solvent-containing crystals there are suitable polar solvents, for example water, aliphatic alcohols, for example methanol, ethanol; amines, for example tertiary amines. The solvent is preferably water. The content of solvent (water) is from 2 to 8% by weight, preferably from 4 to 6% by weight.

In the preparation process there form first of all solvent-containing (water-containing) crystalline isomeric mixtures of the compounds of formulae Ia and IIa, from which solvent-free isomeric mixtures are formed by drying using drying agents.

The isomeric mixtures may contain the meta-para compound and the para-para compound in any ratio by weight. However, preference is given to an isomeric mixture having a content of para-para compound of from 99.9 to 25% by weight and having a content of meta-para compound of from 0.1 to 75% by weight. Special preference is given to an isomeric mixture having a content of para-para compound of from 99.9 to 70% by weight and having a content of meta-para compound of from 0.1 to 30% by weight.

The preparation of the isomeric mixture is carried out according to the following scheme:
a) Friedel-Crafts acylation

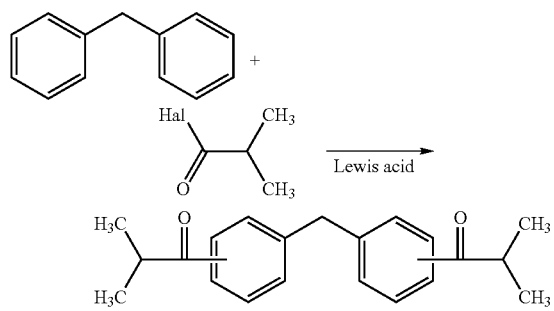

b) chlorination to bis(α-chloroisobutyryl)diphenylmethane,
c) hydrolysis to bis(α-hydroxyisobutyryl)diphenylmethane,
d) further processing to the solvent-containing crystalline isomeric mixture,
e) where appropriate, drying to form the solvent-free crystalline isomeric mixture.

The preparation of the ketone is carried out by Friedel-Crafts acylation, wherein diphenylmethane is reacted with isobutyric acid halide in the presence of a Lewis acid. The known Friedel-Crafts catalysts are suitable, for example aluminium chloride, aluminium bromide, zinc chloride, tin chloride, iron(III) chloride, bismuth chloride or boron trifluoride. Aluminium chloride is preferred.

In the present Friedel-Crafts reaction, it Is possible first to bring the aromatic compound and the catalyst together and to add the acid halide thereto, as described in DE-OS 30 08 411 A1 (1980) of Merck.

It is, however, also possible first to bring the aromatic compound and the acid halide together and to add the catalyst.

It has been found that the sequence of addition of the reagents is critical to the success of the reaction. The best yields are obtained when the aromatic compound and the acid halide are first brought together and the catalyst, preferably aluminium chloride, is slowly added thereto.

Suitable solvents are any solvents that are inert under the indicated reaction conditions, for example ethylene chloride, trichloroethylene, methylene chloride, tetrachloroethane, chlorobenzene, bromobenzene, dichlorobenzene, cyclohexane, methylcyclohexane, carbon disulfide, nitromethane, nitroethane, nitropropane and nitrobenzene. Preference is given to chlorobenzene or ortho-dichlorobenzene.

The reaction temperature is from −20° C. to 20° C., preferably from 0° C. to 10° C., especially from 0° C. to 5° C.

For the reaction there is used an excess of acid halide, relative to diphenylmethane, of from 1.8 to 2.8 equivalents, preferably from 2.0 to 2.6 equivalents, especially from 2.2 to 2.4 equivalents. Acid chloride is preferred to acid bromide.

For the reaction there is used an excess of aluminium chloride, relative to diphenylmethane, of from 1.9 to 2.9 equivalents, preferably from 2.0 to 2.7 equivalents, especially from 2.3 to 2.5 equivalents. The excess of aluminium chloride should be at least as great as the excess of acid halide.

In a further variant, the aluminium chloride may first be brought together with the solvent, and the acid halide may be added dropwise in excess at from −20° C. to 10° C., with cooling. The aromatic compound may then slowly be added at from −20° C. to 10° C., with cooling.

The ketone of step (a) is obtained in the form of an isomeric mixture and can be chlorinated directly in step (b) without being isolated. Chlorinating agents are sulfuryl chloride or chlorine gas. The chlorination is preferably carried out by introduction of chlorine gas at a temperature from 20 to 70° C., preferably from 50 to 60° C. It is also possible to carry out bromination with bromine.

Subsequent hydrolysis with aqueous alkali metal hydroxide (step c) yields the crude isomeric mixture consisting of bis[4-(2-hydroxy-2-methyl-propionyl)-phenyl]-methane and [3-(2-hydroxy-2-methyl-propionyl)-phenyl]-[4-(2-hydroxy-2-methyl-propionyl)-phenyl]-methane, dissolved in the organic phase. It is advantageous to use a mixture of methanol and water for carrying out the hydrolysis.

At the core of the process according to the invention is the subsequent further processing of the crude isomeric mixture to form the solvent-containing crystalline isomeric mixture of compounds of formulae Ia and IIa.

The warm organic phase is diluted, where appropriate, with a suitable solvent, for example with toluene, and then a slightly polar solvent, preferably water (approximately 5 to 15% by weight of the amount of end product) is added thereto. The addition of polar solvent effects crystallisation. Seeding may be carried out with water-containing crystals, where appropriate. The crystals are filtered off, washed and dried. The drying temperature should not exceed 35 to 40° C., in order to prevent sintering of the crystals. The resulting crystals are an isomeric mixture of para-para product and meta-para product in a good yield and in a form which is easy to handle.

The crucial step in the process is the addition of polar solvent, preferably water, to the organic phase, as described above. Without the addition of polar solvent, a rubber-like paste forms and no further crystals can be obtained from the mother liquor. A thick syrup is obtained, which may subsequently partly solidify.

A solvent-free isomeric mixture can be prepared by drying with a drying agent. Examples of suitable drying agents are calcium chloride, calcium oxide, calcium sulfate, active aluminium oxide, magnesium sulfate, sodium sulfate, sodium carbonate, molecular sieves and further conventional drying agents. Sodium sulfate and calcium chloride are preferred. To that end, the isomeric mixture is dissolved in a suitable solvent, for example in toluene, and drying agent is added thereto. Evaporation of the solvent yields a viscous oil, which begins to crystallise after some time.

The invention accordingly relates to a process for the preparation of a crystalline isomeric mixture of compounds of formulae Ia and IIa or I and II, which comprises reacting diphenylmethane with isobutyric acid halide in the presence of a Friedel-Crafts catalyst, and chlorinating and hydrolysing the resulting isomeric mixture consisting of bis[4-(2-methyl-propionyl)-phenyl]-methane and [3-(2-methyl-propionyl)-phenyl]-[4-(2-methyl-propionyl)-phenyl]methane, hydrolysis of the isomeric mixture yielding an aqueous phase and an organic phase that comprises the hydrolysis product; wherein further processing of the hydrolysis product comprises the following steps a) addition of from 3 to 20% by weight of polar solvent (water) to the organic phase, crystallisation and isolation of the solvent-containing Isomeric mixture (formulae Ia and IIa)
b) where appropriate, drying of the isomeric mixture obtained in step a) to obtain a solvent-free (water-free) crystalline isomeric mixture.

In the isolation of the solvent-containing isomeric mixture (step a), the filtrate may, after removal of the crystalline para-para compound by filtration, be subjected to steam distillation in order to remove the solvent. An oil consisting mainly of the meta-para compound is obtained. That oil is likewise suitable as a photoinitiator.

The preparation of the pure para-para compound of formula II in crystalline form is carried out by fractional crystallisation. To that end, for example, the isomeric mixture obtained after the Friedel-Crafts acylation in the first step is isolated by crystallisation. Purification by crystallisation is also carried out in the second step of chlorination (or bromination). As a result of the crystallisations, the relative proportions of the isomers are increasingly shifted in favour of the para-para compound, so that virtually pure para-para compound is obtained.

The preparation of the pure meta-para compound of formula I is carried out at the ketone stage by crystallisation of the para-para compound. As a result, the meta-para compound [3-(2-methyl-propionyl)-phenyl]-[4-(2-methyl-propionyl)-phenyl]-methane becomes concentrated in the mother liquor and can be obtained from the mother liquor by separation by means of HPLC. The chlorination (or bromination), hydrolysis and further processing are carried out as described above.

The novel compounds of formula I or IIa and the isomeric mixtures (formulae Ia and IIa or I and II) are suitable quite generally as photoinitiators.

The invention accordingly relates also to a composition comprising
(A) at least one ethylenically unsaturated compound,
(B) a photoinitiator of formula I, II or IIa or an isomeric mixture of compounds of formulae Ia and IIa or I and II,
(C) optionally a film-forming binder based on a thermoplastic or thermocurable resin;
(D) optionally, further additives,
(E) optionally, further photoinitiators and coinitiators.

The compounds of formulae I, Ia, II and IIa and their isomeric mixtures are suitable, inter alia, as photoinitiators for ethylenically unsaturated compounds containing at least one amino-acrylate.

The invention accordingly relates also to a composition comprising
(A) an ethylenically unsaturated compound containing at least one aminoacrylate,
(B) a photoinitiator of formula I, II or IIa or an isomeric mixture of compounds of formulae Ia and IIa or I and II,
(C) optionally a film-forming binder based on a thermoplastic or thermocurable resin;
(D) optionally, further additives,
(E) optionally, further photoinitiators and coinitiators.

Suitable Ethylenically Unsaturated Compounds (A)

The unsaturated compounds (A) may contain one or more olefinic double bonds. They may be low molecular weight (monomeric) or higher molecular weight (oligomeric).

Examples of monomers having a double bond are alkyl and hydroxyalkyl acrylates and methacrylates, e.g. methyl, ethyl, butyl, 2-ethylhexyl and 2-hydroxyethyl acrylate, isobornyl acrylate, and methyl and ethyl methacrylate. Further examples are acrylonitrile, acrylamide, methacrylamide, N-substituted (meth)acrylamides, vinyl esters, such as vinyl acetate, vinyl ethers, such as isobutyl vinyl ether, styrene, alkyl- and halo-styrenes, N-vinylpyrrolidone, vinyl chloride and vinylidene chloride.

Examples of monomers having a plurality of double bonds are ethylene glycol diacrylate, propylene glycol diacrylate, neopentyl glycol diacrylate, hexamethylene glycol diacrylate and bisphenol A diacrylate, 4,4'-bis(2-acryloyloxyethoxy)diphenylpropane, trimethylolpropane triacrylate, pentaerythritol triacrylate and pentaerythritol tetraacrylate, vinyl acrylate, divinylbenzene, divinyl succinate, diallyl phthalate, triallyl phosphate, triallyl isocyanurate and tris(2-acryloylethyl)isocyanurate.

Examples of higher molecular weight (oligomeric) polyunsaturated compounds are acrylated epoxy resins, acrylated or vinyl-ether- or epoxy-group-containing polyesters, polyurethanes and polyethers.

Further examples of unsaturated oligomers are unsaturated polyester resins, which are usually produced from maleic acid, phthalic acid and one or more diols and have molecular weights of about from 500 to 3000. In addition it is also possible to use vinyl ether monomers and oligomers, and also maleate-terminated oligomers having polyester, polyurethane, polyether, polyvinyl ether and epoxide main chains. Combinations of vinyl-ether-group-carrying oligomers and polymers, as described in WO 90/01512, are especially suitable, but copolymers of monomers functionalised with vinyl ether and maleic acid also come into consideration.

Also suitable are compounds having one or more free-radical-polymerisable double bonds. The free-radical-polymerisable double bonds in such compounds are preferably in the form of (meth)acryloyl groups. Here and in the following, (meth)acryloyl and (meth)acrylic mean acryloyl and/or methacryloyl, and acrylic and/or methacrylic, respectively. At least two polymerisable double bonds in the form of (meth)acryloyl groups are preferably contained in the molecule. The compounds in question may be, for example, (meth)acryloyl-functional oligomeric and/or polymeric compounds of poly(meth)acrylate. The number-average molar mass of that compound may be, for example, from 300 to 10 000, preferably from 800 to 10 000, The compounds preferably containing free-radical-polymerisable double bonds in the form of (meth)acryloyl groups can be obtained by customary methods, for example by reaction of poly(meth)acrylates with (meth)acrylic acid. These and further preparation methods are described in the literature and known to the person skilled in the art.

Such unsaturated oligomers can also be termed prepolymers.

Functional Polymers:

It is also possible to use as component (A) unsaturated acrylates having reactive functional groups. The reactive functional group may be selected, for example, from a hydroxy, thiol, isocyanate, epoxide, anhydride, carboxy, amino and blocked amino group. Examples of unsaturated acrylates containing OH groups are hydroxyethyl acrylates, hydroxybutyl acrylates and also glycidyl acrylates.

Examples of suitable monomers which are normally used to form the backbone (the base polymer) of such functionalised acrylate and methacrylate polymers are, for example, acrylate, methyl acrylate, methyl methacrylate, ethyl acrylate, ethyl methacrylate, n-butyl acrylate, n-butyl methacrylate, isobutyl acrylate, isobutyl methacrylate, 2-ethylhexyl acrylate, 2-ethylhexyl methacrylate, etc. In addition, suitable amounts of functional monomers are copolymerised during the polymerisation in order thus to obtain the functional polymers. Acid-functionalised acrylate or methacrylate polymers are obtained with the aid of acid-functional monomers such as acrylic acid and methacrylic acid. Hydroxy-functional acrylate or methacrylate polymers are obtained from hydroxy-functional monomers, such as 2-hydroxyethyl methacrylate, 2-hydroxypropyl methacrylate, 3,4-dihydroxybutyl methacrylate, or from acrylates which are derived from glycerol derivatives. Epoxy-functionalised acrylate or methacrylate polymers are obtained with the aid of epoxy-functional monomers such as glycidyl methacrylate, 2,3-epoxybutyl methacrylate, 3,4-epoxybutyl methacrylate, 2,3-epoxycyclohexyl methacrylate, 10,11-epoxyundecyl methacrylate, etc. Likewise, isocyanate-functionalised polymers, for example, can be produced from isocyanate-functionalised monomers, for example meta-isopropenyl-α,α-dimethylbenzyl isocyanate. Amino-functionalised polymers are, for example, polyacrylamides, and nitrile-group-containing polymers are, for example, polyacrylonitriles.

Esters

Especially suitable are, for example, esters of ethylenically unsaturated mono- or polyfunctional carboxylic acids and polyols or polyepoxides, and polymers having ethylenically unsaturated groups in the chain or in side groups, e.g. unsaturated polyesters, polyamides and polyurethanes and copolymers thereof, alkyd resins, polybutadiene and butadiene copolymers, polyisoprene and isoprene copolymers, polymers and copolymers having (meth)acrylic groups in side chains, and also mixtures of one or more such polymers.

Examples of suitable mono- or poly-functional unsaturated carboxylic acids are acrylic acid, methacrylic acid, crotonic acid, itaconic acid, cinnamic acid, maleic acid, fumaric acid, itaconic acid, and unsaturated fatty acids such as linolenic acid and oleic acid. Acrylic and methacrylic acid are preferred.

It is also possible, however, to use saturated di- or poly-carboxylic acids in admixture with unsaturated carboxylic acids. Examples of suitable saturated di- or poly-carboxylic acids include, for example, tetrachlorophthalic acid, tetrabromophthalic acid, phthalic anhydride, adipic acid, tetrahydrophthalic acid, isophthalic acid, terepthalic acid, trimellitic acid, heptanedicarboxylic acid, sebacic acid, dodecanedicarboxylic acid, hexahydrophthalic acid, etc.

Suitable polyols are aromatic and, especially, aliphatic and cycloaliphatic polyols. Examples of aromatic polyols are hydroquinone, 4,4'-dihydroxydiphenyl, 2,2-di(4-hydroxyphenyl)propane, and novolaks and resols. Examples of polyepoxides are those based on the said polyols, especially the aromatic polyols and epichlorohydrin. Also suitable as polyols are polymers and copolymers that contain hydroxyl groups in the polymer chain or in side groups, e.g. polyvinyl alcohol and copolymers thereof or polymethacrylic acid hydroxyalkyl esters or copolymers thereof. Further suitable polyols are oligoesters having hydroxyl terminal groups.

Examples of aliphatic and cycloaliphatic polyols include alkylenediols having preferably from 2 to 12 carbon atoms, such as ethylene glycol, 1,2- or 1,3-propanediol, 1,2-, 1,3- or 1,4-butanediol, pentanediol, hexanediol, octanediol, dodecanediol, diethylene glycol, triethylene glycol, polyethylene glycols having molecular weights of preferably from 200 to 1500, 1,3-cyclopentanediol, 1,2-, 1,3- or 1,4-cyclohexanediol, 1,4-dihydroxymethylcyclohexane, glycerol, tris(β-hydroxyethyl)amine, trimethylolethane, trimethylolpropane, pentaerythritol, dipentaerythritol and sorbitol.

The polyols may be partially or fully esterified by one or by different unsaturated carboxylic acid(s), it being possible for the free hydroxyl groups in partial esters to be modified, for example etherified, or esterified by other carboxylic acids.

Examples of Esters are:

trimethylolpropane triacrylate, trimethylolethane triacrylate, trimethylolpropane trimethacrylate, trimethylolethane trimethacrylate, tetramethylene glycol dimethacrylate, triethylene glycol dimethacrylate, tetraethylene glycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentaacrylate, dipentaerythritol hexaacrylate, tripentaerythritol octaacrylate, pentaerythritol dimethacrylate, pentaerythritol trimethacrylate, dipentaerythritol dimethacrylate, dipentaerythritol tetramethacrylate, tripentaerythritol octamethacrylate, pentaerythritol diitaconate, dipentaerythritol trisitaconate, dipentaerythritol pentaitaconate, dipentaerythritol hexaitaconate, ethylene glycol diacrylate, 1,3-butanediol diacrylate, 1,3-butanediol dimethacrylate, 1,4-butanediol diitaconate, sorbitol triacrylate, sorbitol tetraacrylate, pentaerythritol-modified triacrylate, sorbitol tetramethacrylate, sorbitol pentaacrylate, sorbitol hexaacrylate, oligoester acrylates and methacrylates, glycerol di- and tri-acrylate, 1,4-cyclohexane diacrylate, bisacrylates and bismethacrylates of polyethylene glycol having a molecular weight of from 200 to 1500, and mixtures thereof.

The following esters are also suitable: dipropylene glycol diacrylate, tripropylene glycol diacrylate, 1,6-hexanediol diacrylate, glycerol ethoxylate triacrylate, glycerol propoxylate triacrylate, trimethylolpropane ethoxylate triacrylate, trimethylolpropane propoxylate triacrylate, pentaerythritol ethoxylate tetraacrylate, pentaerythritol propoxylate triacrylate, pentaerythritol propoxylate tetraacrylate, neopentyl glycol ethoxylate diacrylate, neopentyl glycol propoxylate diacrylate.

Amides

Also suitable as component (A) are the amides of identical or different unsaturated carboxylic acids and aromatic, cycloaliphatic and aliphatic polyamines having preferably from 2 to 6, especially from 2 to 4, amino groups. Examples of such polyamines are ethylenediamine, 1,2- or 1,3-propylenediamine, 1,2-, 1,3- or 1,4-butylenediamine, 1,5-pentylenediamine, 1,6-hexylenediamine, octylenediamine, dodecylenediamine, 1,4-diaminocyclohexane, isophoronediamine, phenylenediamine, bisphenylenediamine, di-β-aminoethyl ether, diethylenetriamine, triethylenetetramine and di(β-aminoethoxy)- and di(β-aminopropoxy)-ethane. Further suitable polyamines are polymers and copolymers which may have additional amino groups in the side chain and oligoamides having amino terminal groups. Examples of such unsaturated amides are: methylene bisacrylamide, 1,6-hexamethylene bisacrylamide, diethylenetriamine trismethacrylamide, bis(methacrylamidopropoxy)ethane, β-methacrylamidoethyl methacrylate and N-[(β-hydroxyethoxy)ethyl]-acrylamide.

Suitable unsaturated polyesters and polyamides are derived, for example, from maleic acid and diols or diamines. The maleic acid may have been partially replaced by other dicarboxylic acids. They may be used together with ethylenically unsaturated comonomers, e.g. styrene. The polyesters and polyamides may also be derived from dicarboxylic acids and ethylenically unsaturated diols or diamines, especially from those having longer chains of e.g. from 6 to 20 carbon atoms. Examples of polyurethanes are those composed of saturated diisocyanates and unsaturated diols or unsaturated diisocyanates and saturated diols.

Aminoacrylates as Especially Suitable Components (A)

Especially suitable components (A) are acrylates which have been modified by reaction with primary or secondary amines, as described, for example, in U.S. Pat. No. 3,844,916 of Gaske, in EP 280 222 of Weiss et al., in U.S. Pat. No. 5,482,649 of Meixner et al. or in U.S. Pat. No. 5,734,002 of Reich et al., Such amine-modified acrylates are also termed aminoacrylates. Aminoacrylates are obtainable, for example, under the name EBECRYL 80, EBECRYL 81, EBECRYL 83, EBECRYL 7100 from UCB Chemicals, under the name Laromer PO 83F, Laromer PO 84F, Laromer PO 94F from BASF, under the name PHOTOMER 4775 F, PHOTOMER 4967 F from Cognis or under the name CN501, CN503, CN550 from Cray Valley.

The photopolymerisable compounds (A) can be used alone or in any desired mixtures.

Component (C)

Component (C) is, for example, generally a film-forming binder based on a thermoplastic or thermocurable resin, predominantly on a thermocurable resin. Examples thereof are alkyd, acrylic, polyester, phenol, melamine, epoxy and polyurethane resins and mixtures thereof. Examples thereof are described, for example, in Ullmann's Encyclopedia of Industrial Chemistry, 5th Ed., Vol. A18, pp. 368–426, VCH, Weinheim 1991.

Component (C) may be a cold-curable or hot-curable binder, with the addition of a curing catalyst possibly being advantageous. Suitable catalysts that accelerate the full cure of the binder are described, for example, in Ullmann's Encyclopedia of Industrial Chemistry, Vol. A18, page 469, VCH Verlagsgesellschaft, Weinheim 1991.

Examples of particular binders suitable as component (C) are:

1. surface-coating compositions based on cold- or hot-crosslinkable alkyd, acrylate, polyester, epoxy or melamine resins or mixtures of such resins, optionally with the addition of a curing catalyst;
2. two-component polyurethane surface-coating compositions based on hydroxyl-group-containing acrylate, polyester or polyether resins and aliphatic or aromatic isocyanates, isocyanurates or polyisocyanates;
3. two-component polyurethane surface-coating compositions based on thiol-group-containing acrylate, polyester or polyether resins and aliphatic or aromatic isocyanates, isocyanurates or polyisocyanates;
4. single-component polyurethane surface-coating compositions based on blocked isocyanates, isocyanurates or polyisocyanates, which are unblocked during stoving; the addition of melamine resins is also possible;
5. single-component polyurethane surface-coating compositions based on aliphatic or aromatic urethanes or polyurethanes and hydroxyl-group-containing acrylate, polyester or polyether resins;
6. single-component polyurethane surface-coating compositions based on aliphatic or aromatic urethane acrylates or polyurethane acrylates having free amine groups in the urethane structure, and melamine resins or polyether resins, optionally with the addition of a curing catalyst;
7. two-component surface-coating compositions based on (poly)ketimines and aliphatic or aromatic isocyanates, isocyanurates or polyisocyanates;
8. two-component surface-coating compositions based on (poly)ketimines and an unsaturated acrylate resin or a polyacetoacetate resin or a methacrylamidoglycolate methyl ester;
9. two-component surface-coating compositions based on carboxyl- or amino-group-containing polyacrylates and polyepoxides;
10. two-component surface-coating compositions based on anhydride-group-containing acrylate resins and a polyhydroxy or polyamino component;
11. two-component surface-coating compositions based on acrylate-containing anhydrides, and polyepoxides;
12. two-component surface-coating compositions based on (poly)oxazolines and anhydride-group-containing acrylate resins, or unsaturated acrylate resins or aliphatic or aromatic isocyanates, isocyanurates or polyisocyanates;
13. two-component surface-coating compositions based on unsaturated (poly)acrylates and (poly)malonates;
14. thermoplastic polyacrylate surface-coating compositions based on thermoplastic acrylate resins or extrinsically crosslinking acrylate resins, in combination with etherified melamine resins;
15. surface-coating composition systems, especially clear surface-coating compositions, based on malonate-blocked isocyanates with melamine resins (e.g. hexamethoxymethylG16 melamine) as crosslinker (acid-catalysed);
16. UV-curable systems based on oligomeric urethane acrylates and/or acylate acrylates, optionally with the addition of other oligomers or monomers;
17. dual-cure systems, which are first cured thermally and then UV-cured, or vice versa, constituents of the surface-coating composition containing double bonds which can be made to react by UV light and photoinitiators and/or by electron-beam curing.

Further Additives (D)

In addition to the photoinitiator, the photopolymerisable mixtures may optionally comprise further conventional additives (D), depending on the intended use.

Examples thereof are:

antioxidants, optical brighteners, fillers, thermal inhibitors which are intended to prevent premature polymerisation, for example 2,2,6,6-tetramethyl-4-hydroxy-piperidin-1-oxyl(4-hydroxy-TEMPO) and derivatives thereof;

antistatics, wetting agents or flow improvers and adhesion enhancers;

thermal drying or curing catalysts, for example organometallic compounds, amines or/and phosphines;

UV absorbers and light stabilisers, for example those from the group of the 2-(2'-hydroxyphenyl)-benzotriazoles, of the 2-hydroxybenzophenones, esters of unsubstituted or substituted benzoic acids, acrylates, sterically hindered amines, oxalic acid diamides, 2-(2-hydroxy-phenyl)-1,3,5-triazines, phosphites and phosphonites.

Examples of antioxidants, light stabilisers, UV absorbers or optical brighteners are:

$^{RTM}$IRGANOX 1035, 1010, 1076, 1222, $^{RTM}$TINUVIN P, 234, 320, 326, 327, 328, 329, 213, 292, 144, 622LD (commercially available from Ciba Specialty Chemicals), $^{RTM}$ANTIGENE P, 3C, FR, GA-80, $^{RTM}$SUMISORB TM-061 (commercially available from Sumitomo Chemical Industries Co.), $^{RTM}$SEESORB 102, 103, 501, 202, 712, 704 (commercially available from Sypro Chemical Co., Ltd.), $^{RTM}$SANOL LS770 (commercially available from Sankyo Co. Ltd.) $^{RTM}$UVITEX OB, commercially available from Ciba Specialty Chemicals.

Especially advantageous are additions of combinations of sterically hindered piperidine derivatives (HALS) and sterically hindered phenols, for example additions of IRGANOX 1035 and TINUVIN 292, for example in the ratio 1:1.

Photopolymerisation can also be accelerated by addition, as further additives (D), of photosensitisers that shift or broaden the spectral sensitivity. These include especially aromatic carbonyl compounds, for example benzophenone, thioxanthone, including especially isopropylthioxanthone, anthraquinone and 3-acylcoumarin derivatives, terphenyls, styryl ketones, and 3-(aroylmethylene)-thiazolines, camphorquinone and also eosin, rhodamine and erythrosine dyes.

The formulations may also comprise dyes and/or white or coloured pigments. Depending on the intended use, both inorganic and organic pigments may be used.

The additives (D) described above are conventional in the art and accordingly are used in the amounts customary in the art.

It is also possible to add solvents or water to the compositions used in the process according to the invention. Suitable solvents are solvents which are known to the person skilled in the art and are conventional especially in coating technology. Radiation-curable aqueous prepolymer dispersions are obtainable commercially in many variations. They are to be understood as being a dispersion of water and at least one prepolymer dispersed therein.

Further Photoinitiators (E)

It is, of course, also possible to use mixtures with known photoinitiators, for example mixtures with camphorquinone, benzophenone, benzophenone derivatives (e.g. 1-[4-(4-benzoyl-phenylsulfanyl)-phenyl]-2-methyl-2-(toluene-4-sulfonyl)-propan-1-one), acetophenone, acetophenone derivatives, for example α-hydroxycycloalkyl phenyl ketones or dialkoxyacetophenones, α-hydroxy- or α-amino-acetophenones, for example oligo-[2-hydroxy-2-methyl-1-[4-(1-methylvinyl)phenyl]-propanone], 2-hydroxy-2-methyl-1-phenyl-propanone, 2-hydroxy-1-[4-(2-hydroxy-ethoxy)-phenyl]-2-methyl-propan-1-one, 2-methyl-1-[4-(methylthio)phenyl]-2-(4-morpholinyl)-propan-1-one, 2-dimethylamino-2-(4-methylbenzyl)-1-(4-morpholin-4-yl-phenyl)-butan-1-one, 2-benzyl-2-dimethylamino-1-(3,4-dimethoxy-phenyl)-butan-1-one, 2-benzyl-2-dimethylamino-1-(4-morpholin-4-yl-phenyl)-butan-1-one, 2-methyl-1-(4-methylsulfanyl-phenyl)-2-morpholin-4-yl-propan-1-one, 4-aroyl-1,3-dioxolanes, benzoin alkyl ethers and benzil ketals, for example benzil dimethyl ketal, phenyl glyoxalates and derivatives thereof, for example methylbenzoyl formate, dimeric phenyl glyoxalates, for example oxo-phenyl-acetic acid 2-[2-(2-oxo-2-phenyl-acetoxy)-ethoxy]-ethyl ester, peresters, for example benzophenone-tetracarboxylic acid peresters, as described, for example, in EP 126 541, monoacylphosphine oxides, for example (2,4,6-trimethylbenzoyl)-diphenyl-phosphine oxide or phenyl-(2,4,6-trimethylbenzoyl)-phosphinic acid ethyl ester, bisacylphosphine oxides, for example bis(2,6-dimethoxybenzoyl)-(2,4,4-trimethyl-pent-1-yl)phosphine oxide, bis(2,4,6-trimethylbenzoyl)-phenyl-phosphine oxide or bis(2,4,6-trimethylbenzoyl)-(2,4-dipentoxyphenyl)phosphine oxide, trisacylphosphine oxides, halomethyltriazines, for example 2-[2-(4-methoxy-phenyl)-vinyl]-4,6-bis-trichloromethyl-[1,3,5]triazine, 2-(4-methoxy-phenyl)-4,6-bis-trichloromethyl-[1,3,5]triazine, 2-(3,4-dimethoxy-phenyl)-4,6-bis-trichloromethyl-[1,3,5]triazine, 2-methyl-4,6-bis-trichloromethyl-[1,3,5]triazine, hexaarylbisimidazole/coinitiator systems, for example ortho-chlorohexaphenyl-bisimidazole together with 2-mercaptobenzthiazole, ferrocenium compounds or titanocenes, for example dicyclopentadienyl bis(2,6-difluoro-3-pyrrolo-phenyl)titanium, borate photoinitiators or O-acyloxime photoinitiators, as described, for example, in GB 2 339 571.

It is also possible to add cationic photoinitiators, for example benzoyl peroxide (other suitable peroxides are described in U.S. Pat. No. 4,950,581, column 19, lines 17–25), or aromatic sulfonium, phosphonium or iodonium salts, as described, for example, in U.S. Pat. No. 4,950,581, column 18, line 60 to column 19, line 10.

An example of an iodonium salt is (4-isobutyl-phenyl)-4-methylphenyl-iodonium hexafluorophosphate.

Maleimide derivatives, as described, for example, in U.S. Pat. No. 6,153,662 or U.S. Pat. No. 6,150,431 of First Chemicals, may also be present. Examples which may be mentioned are N-(2-trifluoromethylphenyl)maleimide and N-(2-tert-butylphenyl)maleimide.

The photopolymerisable compositions comprise the photoinitiator advantageously in an amount from 0.05 to 15% by weight, preferably from 0.1 to 8% by weight, based on the composition. The indicated amount of photoinitiator relates to the sum of all added photoinitiators when mixtures thereof are used, that is to say both to photoinitiator (B) and to photoinitiators (B)+(E).

Use

The photocurable compositions according to the invention are suitable for various purposes, for example for overprint coatings, for printing inks, especially flexographic printing inks, for clear coats, white coats or colour-pigmented coats, e.g. for wood or metal; for powder coatings, as coating materials for substrates of all kinds, e.g. wood, textiles, paper, ceramics, glass, glass fibres, plastics such as polyester, polyethylene terephthalate, polyolefins or cellulose acetate, especially in the form of films, and also for metals such as Al, Cu, Ni, Fe, Zn, Mg or Co and GaAs, Si or $SiO_2$, to which there is to be applied a protective layer or an image by image-wise exposure.

Examples of metal coatings are the coating of sheet metals and tubes, cans or bottle tops, as a finishing lacquer for applications in the automotive industry.

Examples of the photocuring of paper coatings are the colourless coating of labels or book covers.

The compounds according to the invention can also be used in the form of an aqueous dispersion, for example from 0.5 to 5%, preferably from 0.5 to 2%, in polymer dispersions, for example in water-containing polyurethane dispersions, so-called PUD's.

The photopolymerisable compositions may also be used as daylight-curable paints for marking structures and roads, for photographic reproduction processes, for holographic recording materials, for image-recording processes or in the production of printing plates that can be developed using organic solvents or using aqueous-alkaline media, for the production of masks for screen printing, as dental filling compounds, as adhesives, as pressure-sensitive adhesives, as laminating resins, as etch resists or permanent resists, both liquid and dry films, as photostructurable dielectrics, and as solder masks for electronic circuits, as resists in the production of colour filters for any type of display screen or in the creation of structures during the manufacture of plasma displays and electroluminescent displays, in the production of optical switches, optical gratings (interference gratings), in the manufacture of three-dimensional articles by bulk curing (UV curing in transparent moulds) or according to the stereolithography process, as described, for example, in U.S. Pat. No. 4,575,330, in the manufacture of composite materials (e.g. styrene polyesters which may include glass fibres and/or other fibres and other adjuvants) of gel coats and thick-layered compositions, in the coating or sealing of electronic components or as coatings for optical fibres. The compositions are also suitable for the production of optical lenses, e.g. contact lenses or Fresnel lenses, and also in the manufacture of medical apparatus, aids or implants. The compositions can also be used for the preparation of gels having thermotropic properties. Such gels are described e.g. in DE 197 00 064 and EP 678 534.

A preferred field of application is overprint coatings. These typically consist of ethylenically unsaturated compounds such as oligomeric and/or monomeric acrylates and amino-acrylates. Suitable compounds are listed under "Compound (A)". The compounds and mixtures according to the invention are especially effective in overprint coatings of small layer thickness (from 5 to 10 μm).

A further preferred field of application is UV-curable flexographic printing inks. These likewise consist of ethylenically unsaturated compounds (A) and also comprise UV flexo-resin binders as well as further additives, for example flow improvers and coloured pigments.

A further preferred field of application is powder coatings. The powder coatings may be based on solid resins and monomers containing reactive double bonds (compounds (A)), for example maleates, vinyl ethers, acrylates, acrylamides and mixtures thereof. The powder coatings may also comprise binders, as are described, for example, in DE 4 228 514 and EP 636 669. The UV-curable powder coatings may also comprise white or coloured pigments.

A further preferred field of application are powder coating compositions applied to substrates that are not heat-sensitive, for example to metals (automotive coatings), in said field of application it is also possible to provide "dual cure" powder coating formulations using the photoinitiators according to the invention. Such formulations are known to the person skilled in the art and are both thermally cured and UV-cured. Such formulations can be found, for example, in U.S. Pat. No. 5,922,473.

A further preferred field of application is dispersions.

Suitable dispersants are all surface-active compounds, preferably anionic and non-ionic surfactants, as well as polymeric dispersants. Examples of dispersants which may be used according to the invention include the following classes of compound:

1. Anionic Surfactants
1.1 lignosulfonates,
1.2 dialkyl sulfosuccinates,
1.3 sulfated or sulfonated fatty acids or fatty acid esters of fatty acids,
1.4 reaction products of ethylene oxide and/or propylene oxide with saturated or unsaturated fatty acids, fatty alcohols, fatty amines, alicyclic alcohols or aliphatic-aromatic hydrocarbons which have been esterified in the terminal position by an inorganic oxygen-containing acid or a polybasic carboxylic acid.

The anionic dispersants are normally in the form of their alkali metal salts, their ammonium salts or their water-soluble amine salts. Low-electrolyte grades are advantageously used.

2. Non-ionic Surfactants

Ethylene oxide adducts from the class of the addition products of ethylene oxide with higher fatty acids, saturated or unsaturated fatty alcohols, fatty amines, mercaptans, fatty acid amides, fatty acid alkylol amides or fatty amines or with alkylphenols or with alkylthiophenols, with from 5 to 100 mol of ethylene oxide being used per mol of the mentioned compounds, as well as ethylene oxide-propylene oxide block polymers and ethylene-diamine-ethylene oxide-propylene oxide adducts.

These include: 2.1 reaction products of saturated and/or unsaturated fatty alcohols having from 8 to 20 carbon atoms with from 20 to 100 mol of ethylene oxide per mol of alcohol, preferably saturated linear $C_{16}$–$C_{18}$ alcohols with from 25 to 80 mol, especially 25 mol, of ethylene oxide per mol of alcohol;
2.2 reaction products of saturated and/or unsaturated fatty acids having from 8 to 20 carbon atoms with from 5 to 20 mol of ethylene oxide per mol of acid;
2.3 reaction products of alkylphenols having from 7 to 12 carbon atoms with from 5 to 25 mol of ethylene oxide per mol of phenolic hydroxy group, preferably mono- or dialkylphenols with from 10 to 20 mol of ethylene oxide per mol of phenolic hydroxyl group;
2.4 reaction products of saturated and/or unsaturated fatty acid amides having up to 20 carbon atoms with from 5 to 20 mol of ethylene oxide per mol of acid amide, preferably oleic acid amides with from 8 to 15 mol of ethylene oxide per mol of acid amide;
2.5 reaction products of saturated and/or unsaturated fatty amines having from 8 to 20 carbon atoms with from 5 to 20 mol of ethylene oxide per mol of amine, preferably oleylamines with from 8 to 15 mol of ethylene oxide per mol of amine;
2.6 ethylene oxide-propylene oxide block polymers having from 10 to 80% ethylene oxide and molecular weights from 1000 to 80 000;
2.7 ethylene oxide-propylene oxide adducts with ethylene-diamine.

3. Polymeric Dispersants and Protective Colloids

Suitable polymeric dispersants are, for example, amphiphilic copolymers, block copolymers or graft or comb polymers, especially those based on acrylic acid, methacrylic acid or salts thereof, hydroxyalkyl(meth)acrylic acid, aminoalkyl(meth)acrylic acid or salts thereof, 2-acrylamido-2-methylpropanesulfonic acid (AMPS) or salts thereof, maleic anhydride or salts thereof, (meth)acrylamide or substituted (meth)acrylamides, vinyl heterocycles, for example vinylpyrrolidone, vinylimidazole, as well as amphiphilic polymers containing segments of PEO or EO/PO copolymers.

Examples of suitable protective colloids are polyvinyl alcohol, polyvinylpyrrolidone or its copolymers.

Also suitable are copolymers of synthetic monomers, especially of monomers having carboxyl groups, for example copolymers of 2-vinylpyrrolidone with 3-vinylpropionic acid or maleic acid copolymers and salts thereof.

Preferred dispersants are polymers based on maleic anhydride, polyvinyl alcohol or modified polyacrylates, for example the alkali metal salts, especially the sodium salts, of carboxylic acid copolymers or polyvinyl alcohol.

The substrates can be coated by applying a liquid composition, a solution or a suspension to the substrate. The choice of solvent and its concentration are governed chiefly by the nature of the composition and the coating method. The solvent should be inert, that is to say it should not enter into any chemical reaction with the components, and it should be capable of being removed again on drying after the coating operation. Suitable solvents include, for example, ketones, ethers and esters, such as methyl ethyl ketone, isobutyl methyl ketone, cyclopentanone, cyclohexanone, N-methylpyrrolidone, dioxane, tetrahydrofuran, 2-methoxyethanol, 2-ethoxyethanol, 1-methoxy-2-propanol, 1,2-dimethoxyethane, ethyl acetate, n-butyl acetate and ethyl 3-ethoxypropionate.

The formulation is applied uniformly to a substrate by means of known coating methods, for example by spin-coating, immersion, knife coating, curtain pouring, brush application or spraying, especially by electrostatic spraying and reverse-roll coating, and also by electrophoretic deposition. It is also possible to apply the photosensitive layer to a temporary flexible support and then coat the final substrate by transferring the layer via lamination. Examples of types of application are to be found, for example, in Ullmann's Encyclopedia of Industrial Chemistry, 5th Edition, Vol. A18, pp. 491–500.

The amount applied (layer thickness) and the nature of the substrate (layer support) are dependent on the desired field of application. The range of dry layer thicknesses generally includes values from about 0.1 µm to more than 100 µm.

The photosensitivity of the compositions according to the invention usually extends from approximately 200 nm to within the IR range. Suitable radiation is present, for example, in sunlight or light from artificial light sources. Accordingly a large number of the most varied kinds of light source may be used. Both point sources and planiform radiators (lamp carpets) are suitable. Examples are: carbon arc lamps, xenon arc lamps, medium-pressure, high-pressure and low-pressure mercury radiators, doped, where appropriate, with metal halides (metal halide lamps), microwave-excited metal vapour lamps, excimer lamps, superactinic fluorescent tubes, fluorescent lamps, argon incandescent lamps, flash lamps, e.g. high-energy flash lamps, photographic floodlight lamps, light-emitting diodes (LED), electron beams and X-rays. The distance between the lamp and the substrate to be exposed may vary according to the intended use and the type and strength of the lamp and may be, for example, from 2 cm to 150 cm. Especially suitable are laser light sources, for example excimer lasers, such as Krypton-F lasers for exposure at 248 nm. Lasers in the visible range may also be used.

As already mentioned, curing in the process according to the invention can be carried out simply by irradiation with electromagnetic radiation. Depending on the composition of the formulation to be cured, however, thermal curing before, during or after the irradiation is advantageous.

Thermal curing is carried out by methods known to the person skilled in the art. In general, the curing is carried out in an oven, e.g. a circulating air oven, on a hot plate or by irradiation with IR lamps. Unassisted curing at room tempeature is also possible, depending on the binder system used. The curing temperatures are generally between room temperature and 150° C., for example from 25 to 150° C. or from 50 to 150° C. In the case of powder coatings or coil coatings, the curing temperatures may be even higher, e.g. up to 350° C.

The invention relates also to a process for the production of a scratch-resistant durable surface, wherein a composition comprising at least one aminoacrylate and a photoinitiator of formula I, II or IIa or an isomeric mixture of compounds of formulae Ia and IIa or I and II is applied to a support; and curing of the formulation is carried out either only by means of irradiation with electromagnetic radiation having a wavelength of from 200 nm to within the IR range, or by irradiation with electromagnetic radiation and prior, simultaneous and/or subsequent action of heat.

The invention relates also to the use of the above-described composition and to a process for the production of pigmented and non-pigmented surface coatings, overprint coatings, formulations for printing inks, powder coatings, dispersions, gel coats, composite materials or glass fibre cable coatings.

The invention relates also to a coated substrate which is coated on at least one surface with a composition as described above.

The following Examples further illustrate the invention:

EXAMPLE 1

Preparation of a Crystalline Isomeric Mixture (Formulae Ia and IIa) Containing Water of Crystallisation 1.1) Friedel-Crafts Reaction 109.4 g (0.65 mol) of diphenylmethane, 159.3 g (1.495 mol) of isobutyric acid chloride and 150 ml of 1,2-dichlorobenzene are combined and cooled to 5–0° C. In the course of about four hours, 208.0 g (1.56 mol) of aluminium chloride are added in small portions at an internal temperature of 5–0° C. HCl gas is evolved. Stirring is then carried out for about 16 hours at an internal temperature of 0–5° C. At the end of that period, all the aluminium chloride has dissolved. The dark-red reaction mixture is then poured onto ice and water and stirred to complete the reaction. The two phases are separated in a separating funnel. The organic phase is washed with water and then concentrated for a short time in a vacuum rotary evaporator at about 60° C. and about 25 mbar. 403.1 g of a yellow liquid are obtained. The product, an isomeric mixture with bis[4-(2-methyl-propionyl)-phenyl]-methane as the main component, is used in the next reaction without being purified further. Excluding the solvent 1,2-dichlorobenzene, 87.3% p,p-isomer, 11.4% m,p-isomer, 0.66% m,m-isomer and 0.60% p-mono compound are found in the GC and $^1$H-NMR spectrum.

1.2) Enol Chlorination 403.1 g (0.65 mol) solution of the isomeric mixture of bis[4-(2-methyl-proplonyl)-phenyl]-methane with [3-(2-methyl-propionyl)-phenyl]-[4-(2-methyl-proplonyl)-phenyl]-methane from the Friedel-Crafts reaction are heated to 55–60° C. by means of an oil bath. 92.2 g (1.30 mol) of chlorine gas are then introduced through a glass frit at 55–60° C., with thorough stirring, more rapidly at the beginning and only slowly at the end. HCl gas is evolved. The duration of the introduction is about 6 hours. 441.5 g of a yellowish liquid are obtained. The product, an isomeric mixture with bis[4-(2-chloro-2-methyl-propionyl)-phenyl]-methane as the main component, is used in the next reaction without being purified further. Excluding the solvent 1,2-dichlorobenzene, about 87% p,p-isomer and about 12% m,p-isomer are found in the $^1$H-NMR spectrum.

1.3) Hydrolysis

Variant 1.3a

Rapid Crystallisation for Working-up of the Hydrolysis Product 208.0 g (1.56 mol) of NaOH concentrated to 30% and 208 ml of deionised water and 205.7 g of methanol are combined. There are then added dropwise at 50° C. in a period of about one hour, with thorough stirring, 441.5 g (0.65 mol) of a solution, in 1,2-dichlorobenzene, of the isomeric mixture of bis[4-(2-chloro-2-methyl-propionyl)-phenyl]-methane with [3-(2-chloro-2-methyl-propionyl)-phenyl]-[4-(2-chloro-2-methyl-propionyl)-phenyl]-methane from the chlorination reaction, additionally diluted with 102.8 g of methanol. The internal temperature slowly rises to 55–60° C. The alkaline mixture (about pH 12) is then stirred for about three to four hours at 55–60° C. The conversion is checked with a GC sample and a $^1$H-NMR sample. The mixture is then cooled to 45° C. and adjusted dropwise to a pH of about 2–3 with about 63.5 g of 16% hydrochloric acid. The colour of the emulsion changes from a strong yellow to yellow. The mixture is then stirred for about 30 minutes. When the hydrolysis is complete, the reaction mixture is neutralised with a small amount of dilute sodium hydroxide solution. The two phases are separated at about 50° C. in a separating funnel. 200 ml of water are added to the organic phase, which is then stirred and separated off again. The organic phase is the solution of an isomeric mixture with bis[4-(2-hydroxy-2-methyl-propionyl)-phenyl)-methane as the main component. About 88% p,p-isomer and about 11% m,p-isomer are found in the $^1$H-NMR spectrum. The warm organic phase is diluted with solvent (400 ml of toluene), and a small amount of water (about 23 g of water, about 10% of the amount of end product) is added thereto. The solution is seeded at 40–35° C. with water-containing crystals and is later cooled after the crystallisation. The thick suspension is filtered and washed with toluene and hexane in order to displace the 1,2-dichlorobenzene. The crystals are dried in vacuo to constant weight. 177.7 g of white crystals containing water of crystallisation are obtained. This corresponds to a yield of 76.3% of theory (358.44) over all three reaction steps. The crystals of the isomeric mixture melt at 68–70° C. and contain 5.02% by weight water. The crystals exhibit an X-ray powder spectrum with the characteristic lines at a 2-theta angle of 6.69; 9.67; 13.95; 15.11; 16.35; 17.57; 19.43; 21.39; 22.17; 23.35; 25.93; 27.11; 27.79; 28.73; 34.83; 41.15. (FIG. 1)

Elemental analysis: (358.44)

| | % C | | % H |
|---|---|---|---|
| calculated: | 70.37 | calculated: | 7.31 |
| found: | 70.35 | found: | 7.37 |

Variant 1.3b

Slow Crystallisation for Working-up of the Hydrolysis Product

The isomeric mixture obtained in Example 1.2 is hydrolysed analogously to Variant 1.3a. About 88% p,p-isomer (bis[4-(2-hydroxy-2-methyl-propionyl)-phenyl]-methane) and about 11% m,p-isomer are found in the GC and $^1$H-NMR spectrum. After separating the organic phase and the aqueous phase, the warm organic phase (about 55° C.) is diluted with 250 ml of toluene, and about 30 g of water are then added thereto. The solution begins to crystallise spontaneously at 36° C., and the temperature rises to 42° C. The suspension, which has thickened, is diluted with 75 ml of toluene and stirred for one hour without cooling. The experiment is left to stand overnight and on the following morning is cooled to 5° C. using an ice-water bath. The cold, thick suspension is filtered and washed with 75 ml of toluene and 140 g of hexane mixture In order to displace the 1,2-dichlorobenzene. The moist filtration product is weighed, 204.5 g of moist white crystals, and halved. A portion of the crystals is immediately dried, a portion of the crystals is subjected to after-treatment. The mother liquor and the solvent used for washing are together concentrated in vacuo. 45.5 g of brown liquid residue are obtained. About 42% p,p-isomer and about 58% m,p-isomer, determined by evaluation of the integrals of the aromatic protons, are found in the $^1$H-NMR spectrum.

The 102.3 g of white crystals are dried in vacuo to constant weight. 88.19 of white, flocculent, voluminous crystals containing water of crystallisation are obtained. This corresponds to a yield of 75.6% of theory (358.44) over all three reaction steps. The crystals of the isomeric mixture melt at 71–74° C. and contain 5.12% by weight water according to Karl Fischer water determination. FIG. 2 shows the X-ray powder spectrum with the characteristic lines at a 2-theta angle of 6.69; 9.69; 14.03; 15.15; 16.41; 17.57; 19.47; 19.75; 21.39; 22.19; 23.33; 25.91; 27.05; 27.79; 28.67; 41.05.

Elemental analysis: (358.44)

| | % C | | % H |
|---|---|---|---|
| calculated: | 70.37 | calculated: | 7.31 |
| found: | 70.24 | found: | 7.39 |

Variant 1.3c

After-treatment

The other half, 102.2 g of moist white crystals, is dissolved with 150 g of toluene and heated for distillation. 68 g of toluene and 15 g of water are distilled off, final temperature about 110° C. in the solution. The solution is slowly cooled and left to stand overnight. On the following morning, all the material is still dissolved. The solution is seeded with water-free crystals, with stirring. It slowly crystallises out. The suspension Is later diluted with 60 g of toluene, then cooled to 5° C., filtered and washed with 90 g of toluene. The white crystals are dried in vacuo to constant weight. 71.7 g of white, hard, compact crystals are obtained. This corresponds to a yield of 64.8% of theory (340.42) over all three reaction steps. The crystals of the isomeric mixture melt at 87–90° C. and contain 2.02% by weight water according to Karl Fischer water determination. The mother liquor and the solvent used for washing are together concentrated in vacuo. 12.3 g of yellowish oil are obtained.

Variant 1d

Change of Solvent Before the Hydrolysis 1 d.2) Enol Chlorination

Analogously to Example 1, the Friedel-Crafts reaction and the enol chlorination are carried out with 1,2-dichlorobenzene as solvent. 460.6 g of a yellowish liquid are obtained. The product, an isomeric mixture with bis[4-(2-chloro-2-methyl-propionyl)-phenyl]-methane as the main component, is freed of the solvent 1,2-dichlorobenzene by means of steam distillation before the next reaction. The head temperature in the distillation is about 95° C. and the distillation lasts about 4 hours. About 145 ml of 1,2-dichlorobenzene are recovered. The residue, a yellowish emulsion, is diluted with 195 g of toluene and separated from the water while still warm. There are obtained 462.7 g of organic phase, which is used in the next reaction without being purified further. Excluding the new solvent toluene, about 87% p,p-isomer and about 12% m,p-isomer are found in the GC and $^1$H-NMR spectrum.

1d.3) Hydrolysis 208.0 g (1.56 mol) of NaOH concentrated to 30% and 208 ml of deionised water and 205.7 g of methanol are combined. The temperature rises to about 38° C. The mixture is then heated to 50° C. by means of an oil bath. There are then added dropwise in a period of about one hour, with thorough stirring, 462.7 g (0.65 mol) of a solution, in toluene, of the isomeric mixture of bis[4-(2-chloro-2-methyl-propionyl)-phenyl]-methane with [3-(2-chloro-2-methyl-propionyl)-phenyl]-[4-(2-chloro-2-methyl-propionyl)-phenyl]-methane from the chlorination reaction, additionally diluted with 103 g of methanol. The internal temperature slowly rises to 55–60° C. The alkaline mixture (about pH 11) is then stirred for about three to four hours at 55–60° C. The conversion is checked with a $^1$H-NMR sample. The mixture is then cooled to 27° C. and adjusted dropwise to a pH of about 1–2 with about 73.4 g of 16% hydrochloric acid. The colour of the emulsion changes from red to reddish. The mixture is then stirred for about 100 minutes at 55–60° C. When the hydrolysis is complete, the reaction mixture is neutralised with about 9.4 g of dilute sodium hydroxide solution (15%). The two phases are separated at about 50° C. in a separating funnel. 200 ml of toluene and 200 ml of water are added to the organic phase, which is then stirred and separated off again. The organic phase is an isomeric mixture with bis[4-(2-hydroxy-2-methyl-propionyl)-phenyl]-methane as the main component. About 88% p,p-isomer and about 11% m,p-isomer are found in the GC and $^1$H-NMR spectrum. The warm organic phase is again diluted with 300 ml of toluene, and then about 30 g of water are added thereto. The solution is seeded at 40–35° C. with water-containing crystals and is later heated to about 50° C. after the crystallisation. The thick suspension is slowly cooled and later cooled further by means of an ice-water bath. It is then filtered and washed with 200 ml of toluene. The white crystals are dried in vacuo to constant weight. 173.1 g of white, voluminous crystals containing water of crystallisation are obtained. This corresponds to a t.q. yield of 74.3% of theory (358.44) over all three reaction steps. The crystals of the isomeric mixture melt at 70.6–71.7° C. and contain 4.8% by weight water according to Karl Fischer water determination.

The mother liquor and the solvent used for washing are together concentrated in vacuo. 47.7 g of residue, a reddish viscous oil, are obtained.

1d.4) Enol Chlorination

Analogously to Example 1.1 and 1.2, the Friedel-Crafts reaction and the enol chlorination are carried out using 1,2-dichlorobenzene as solvent. 457.2 g of a yellowish liquid are obtained. The product, an isomeric mixture with bis[4-(2-chloro-2-methyl-propionyl]phenyl]-methane as the main component, is freed of the solvent 1,2-dichlorobenzene before the next reaction by means of steam distillation. The head temperature in the distillation is about 95° C. and the distillation lasts about 4 hours. About 150 ml of 1,2-dichlorobenzene are recovered. The residue, a yellowish emulsion, is diluted with 195 g of toluene and separated from the water while still warm. There are obtained 459.7 g of organic phase, which is used in the next reaction without being purified further. Excluding the new solvent toluene, about 87% p,p-isomer and about 12% m,p-isomer are found in the GC and $^1$H-NMR.

1d.5) Hydrolysis 459.7 g (0.65 mol) of a solution, in toluene, of the isomeric mixture of bis[4-(2-chloro-2-methyl-propionyl)-phenyl]-methane with [3-(2-chloro-2-methyl-propionyl)-phenyl]-[4-(2-chloro-2-methyl-propionyl)-phenyl]-methane from the chlorination reaction are introduced into a reaction flask and diluted with 308.5 g of methanol. The mixture is then heated to 50° C. by means of an oil bath. 208.09 (1.56 mol) of NaOH concentrated to 30% are then added dropwise in a period of about one hour, with thorough stirring. The internal temperature slowly rises to 55–60° C. The alkaline mixture (about pH 11) is then stirred for about 3 hours at 55–60° C. The conversion is checked with a $^1$H-NMR sample. The mixture is then cooled to 40° C. and adjusted dropwise to a pH of about 1–2 with about 58.2 g of 16% hydrochloric acid. The colour of the emulsion changes from red to reddish. The mixture is then stirred further for about 2 hours at 55–60° C. When the hydrolysis is complete, the reaction mixture is neutralised with about 4.3 g of dilute sodium hydroxide solution (15%). The two phases are separated at about 50° C. in a separating funnel. 200 ml of toluene and 200 ml of water are added to the organic phase, which is then stirred and separated off again. About 88% p,p-isomer and about 11% m,p-isomer are found in the $^1$H-NMR spectrum. The warm organic phase is diluted again with 300 ml of toluene, and then about 30 g of water are added thereto. The solution begins to crystallise out at 38° C. and is later heated to about 50° C. again after the crystallisation. The suspension is slowly cooled and later cooled further by means of an ice-water bath. It is then filtered and washed with 200 ml of toluene. The white crystals are dried in vacuo to constant weight. 180.5 g of white crystals containing water of crystallisation are obtained. This corresponds to a t.q. yield of 77.5% of theory (358.44) over all three reaction steps. The crystals of the isomeric mixture melt at 72.1–74.7° C. and contain 4.7% by weight water according to Karl Fischer water determination. The overall content of meta-para compound in the crystals is determined indirectly at the end of Example 1 e.

1 d.5a) Purifcation of the Mother Liquor

The mother liquor and the solvent used for washing are together concentrated in vacuo. 40.0 g of a reddish viscous oil are obtained. The oil is purified by means of flash chromatography over silica gel 60 (0.040–0.063 mm) from Merck. A mixture of ethyl acetate:hexane mixture 1:2 is used as eluant. 28.5 g of yellow-reddish oil are isolated as the main fraction. It is a pure product in the thin-layer chromatogram. About 36% p,p-isomer and about 64% m,p-isomer, determined by evaluation of the Integrals of the aromatic protons, are found in the $^1$H-NMR spectrum.

Variant 1 e

Determination of the Distribution of Isomers after Crystallisation

Analogously to Example 1, diphenylmethane is acylated with isobutyric acid chloride in 1,2-dichlorobenzene, the diketone mixture is then chlorinated without intermediate purification, and hydrolysis is finally carried out with sodium hydroxide solution and with the addition of methanol. The distribution of isomers between the para-para compound and the meta-para compound, about 12% meta-para compound, is maintained over all three steps, because no product is separated off until crystallisation. After separation of the aqueous phase, toluene and water are added analogously to Example 1.3b. The solution crystallises out at about 30° C. It is heated again to about 50° C., until almost all the material has dissolved, and the suspension is then stirred while cold. On the following morning, the mixture is cooled to 5° C. by means of an ice-water bath and then filtered after 5 hours. The crystals are washed with toluene and hexane mixture in order to displace the 1,2-dichlorobenzene. The 173.2 g of white crystals are dried in vacuo at about 30° C. to constant weight. 148.4 g of fine-grained white crystals containing water of crystallisation are obtained. This corresponds to a yield of 78.6% of theory (358.44) over all three reaction steps (0.5265 mol). The crystals of the isomeric mixture melt at 71–73° C. and contain 4.6% by weight water according to Karl Fischer water determination. After several weeks, the melting range stabilises at 76.0–77.5° C.

The mother liquor, 528 g of yellowish solution, is concentrated in a vacuum rotary evaporator and then freed of solvent 1,2-dichlorobenzene by means of steam distillation. The head temperature in the distillation is about 95° C. and the distillation lasts about one hour. The oil is separated from the water and then freed of solvent completely at about 60° C. and under a good vacuum (0.5 mbar). 36.79 of thick brownish oil are obtained. About 42% p,p-isomer and about 58% m,p-isomer, determined by evaluation of the integrals of the aromatic protons, are found in the $^1$H-NMR spectrum of the concentrated mother liquor.

The crystals have only a small amount of m,p-isomer in the $^1$H-NMR spectrum. The proportion of meta-para compound in the crystals was for a long time uncertain because of the resonances of the secondary products and the traces of 1,2-dichlorobenzene, which occur at the same locations in the $^1$H-NMR spectrum. Without removal of 1,2-dichlorobenzene by prior steam distillation, the integral for the meta-para isomer in the $^1$H-NMR spectrum is not visible.

In order better to determine and monitor the distribution of isomers between the para-para compound and the meta-para compound in the crystals, a larger sample is recrystallised from toluene and water. The exact procedure is as follows:

A sample of 120.0 g of crystalline product from Example 1e is dissolved in 180 g of toluene at 55° C., and 20 g of water are added thereto. The solution is then allowed to cool slowly, with stirring. It crystallises at about 49° C., with a rise in temperature to about 56° C. It is stirred overnight, without cooling, to complete the reaction and is then cooled to about 5° C. After two hours, filtration through a suction filter is carried out. The filtration product is washed with 30 g of cold toluene and dried in vacuo in a drying cabinet between room temperature and 40° C. There are obtained 118.3 g of hard white crystals, which melt at 74–79° C. The toluenic mother liquor (about 195 g) is concentrated and dried. There remain 1.7 g of yellowish oil, which shows about 60% meta-para compound in the $^1$H-NMR spectrum (300 MHz). This corresponds to 1.0 g of meta-para compound, which corresponds to a content of about 0.85% of meta-para compound in the crystals used. A further analogous recrystallisation of a sample of 100 g of the obtained crystals from toluene and water gives a toluenic filtrate which, after concentration to 4.6 g of colourless oil, shows about 2.0% of meta-para compound in the $^1$H-NMR spectrum. This corresponds to 0.1 g of meta-para compound, which corresponds to a content of about 0.10% of meta-para compound in the crystals used. The two contents of about 0.85% and about 0.10% are added together, and the total content of meta-para compound in the tested crystals is from about 0.9% to about 1.0%. This estimate is now sufficiently accurate.

In an analogous manner, a sample of 120.0 g of crystalline product from Example 1 d.5 is dissolved in 180 g of toluene at 62° C., and 23 g of water are added thereto. The solution is cooled and crystallised in the same manner. The suspension is stirred overnight to complete the reaction, and is then filtered at room temperature. The crystals are washed with 90 g of toluene and dried in vacuo in a drying cabinet between room temperature and 40° C. There are obtained 114.1 g of hard white crystals, which melt at 70–76° C. The toluenic mother liquor is concentrated and dried. There remain 5.1 g of yellowish oil, which shows about 36% meta-para compound in the $^1$H-NMR spectrum (300 MHz). This corresponds to 1.84 g of meta-para compound, which corresponds to a content of about 1.5% meta-para compound, which was extracted from the crystals used. The total content of meta-para compound in the tested crystals is estimated at from about 1.5% to about 1.7%. The direct estimation of the total content of meta-para compound from the $^1$H-NMR spectrum (300 MHz) by evaluation of the integrals of the aromatic protons is no longer reliable with such small amounts.

Variant 1f

Change of solvent after hydrolysis and adjustment of the ratio of isomers in the crystals Analogously to Example 1, diphenylmethane is acylated with isobutyric acid chloride in 1,2-dichlorobenzene, then the diketone mixture is chlorinated without intermediate purification, and hydrolysis is finally carried out with sodium hydroxide solution and with the addition of methanol. The distribution of isomers in the reaction mixture between the para-para compound and the meta-para compound, about 12% meta-para compound, is maintained over all three steps, because no product is separated off until crystallisation. After separation of the aqueous phase, the organic phase, in a modification of Example 1, is subjected to steam distillation at about 95–100° C., and the 1,2-dichlorobenzene is removed. About 154 g of 1,2-dichlorobenzene are recovered. There is obtained a thick yellow oil, which tends to crystallise with water below 60° C. The oil is crystallised with a large amount of water without further solvent. Slow cooling yields moist, light-yellow spherules, which are filtered off and dried in vacuo at about 35–40° C. In the $^1$H-NMR spectrum of the crystals, the distribution of isomers between the para-para compound and the meta-para compound is the same as in the $^1$H-NMR spectrum of a sample of the oil, i.e. about 88% para-para isomer and about 12% meta-para isomer. It no longer contains any 1,2-dichlorobenzene to interfere with the evaluation of the $^1$H-NMR spectrum. The light-yellow crude product is also surprisingly pure in the TLC. There are obtained 222.9 g of yellowish granules, which melt at 63–72° C. This corresponds to a yield of 95.7% over three reaction steps with a starting batch size of 0.65 mol (Example 1f).

From that crude product, by means of controlled crystallisations from water with variously small additions of toluene, it is possible to produce products having selected compositions of the isomers. Accordingly, a portion of the meta-para compound can be filtered off with the variously small amounts of toluene. From the toluenic filtrate and its isomeric composition in the $^1$H-NMR spectrum, as well as the amount of crystals and their isomeric composition in the ¹H-NMR spectrum, it is possible to calculate and confirm the isomeric composition in the crystals more exactly.

A 60 g sample of that yellowish crude product is heated and melted in 90 g of water. 90 g of toluene are added at about 80° C. The mixture is cooled slowly and crystallised, and the suspension is filtered and washed with water. The crystals are dried in vacuo. There are obtained 50 g of slightly yellowish crystals, which melt at 67–72° C. Evaluation of the ¹H-NMR spectrum in the oil from the concentrated filtrate, 7.0 g of yellowish oil, shows about 75% meta-para compound and about 25% para-para compound. On calculating back that loss to the 50 g of crystals, a new content of about 3.9% of meta-para compound in the crystals is determined. This is confirmed by evaluation of the ¹H-NMR spectrum of the crystals, which contain about 4% meta-para compound (Example 1fa).

A further 60 g sample of the yellowish crude product is heated and melted in 50 g of water. 40 g of toluene are added at about 80° C. The mixture is cooled slowly and crystallised, and the suspension is filtered and washed with water. The crystals are dried in vacuo. There are obtained 54 g of yellowish crystals, which melt at 66–72° C. Evaluation of the ¹H-NMR spectrum in the oil from the concentrated filtrate, 4.7 g of yellowish oil, shows about 75% meta-para compound and about 25% para-para compound. On calculating back that loss to the 54 g of crystals, a new content of about 6.8% of meta-para compound in the crystals is determined. This is confirmed by evaluation of the ¹H-NMR spectrum of the crystals, which contain about 7% meta-para compound (Example 1fb).

EXAMPLE 2

Preparation of a Water-Free Crystalline Isomeric Mixture from the Corresponding Water-Containing Isomeric Mixture The crystalline starting material from Example 1.3a which is used melts at 68–70° C. and contains 5.02% by weight water. The crystals show an X-ray powder spectrum with the characteristic lines at a 2-theta angle of 6.69; 9.67; 13.95; 15.11; 16.35; 17.57; 19.43; 21.39; 22.17; 23.35; 25.93; 27.11; 27.79; 28.73; 34.83; 41.15. (FIG. 1)

30 g of the isomeric mixture from Example 1.3a are heated to 70° C. In 170 g of toluene, in order to dissolve the product. At 65° C., all the material has dissolved. The few drops of water cannot be separated off in a separating funnel. 10 g of water-free calcium chloride are then added to the toluene solution. Stirring is carried out for one hour at 65° C., followed by filtration. The toluene solution is concentrated in vacuum rotary evaporator and dried under a high vacuum. 25.2 g of yellowish oil are obtained, which begins to crystallise slowly after more than 24 hours. The crystals of the isomeric mixture melt at 89.2–91.2° C. and contain 0.09% by weight water according to Karl Fischer water determination. FIG. 3 shows the X-ray powder spectrum with the characteristic lines at a 2-theta angle of 10.71; 11.19; 16.43; 17.25; 17.87; 21.53; 22.59; 25.99; 28.75.

Elemental analysis of the end sample: (340.42)

|  | % C |  | % H |
|---|---|---|---|
| calculated: | 74.09 | calculated: | 7.11 |
| found: | 73.65 | found: | 7.04 |

EXAMPLE 3

Preparation of bis[4-(2-hydroxy-2-methyl-propionyl)-phenyl]-methane, Compound of Formula IIa or II 3.1) Friedel-Crafts Reaction and Separation 168.2 g (1.0 mol) of diphenylmethane, 245.1 g (2.3 mol) of isobutyric acid chloride and 150 ml of 1,2-dichlorobenzene are combined and cooled to 5–0° C. by means of an ice bath. The acylation is carried out analogously to Example 1.

After working up, the organic phase is washed with water and then concentrated in a vacuum rotary evaporator at about 60° C. and about 25 mbar. The organic phase is then concentrated completely under a high vacuum. There are obtained 395.8 g of a yellow liquid, which still contains some solvent 1,2-dichlorobenzene. This corresponds to a crude yield of 128% of theory. The product is an isomeric mixture with bis[4-(2-methyl-propionyl)-phenyl]-methane as the main component, and 86.7% p,p-isomer, 11.1% m,p-isomer, 0.7% m,m-isomer and 1.5% p-mono compound are found in the ¹H-NMR spectrum, excluding the solvent 1,2-dichlorobenzene. The product is dissolved in 100 ml of hexane and crystallised out in a refrigerator. The crystals are filtered off, washed with cold hexane and dried in vacuo. There are obtained 169 g of white crystals, which are again dissolved in 70 ml of warm hexane. The product crystallises again and is filtered off, washed and dried. There are obtained 160 g of white crystals, which melt at 42–44° C. 97.3% para-para isomer and 2.7% meta-para isomer are now found in the GC and ¹H-NMR spectrum.

The filtrate, about 350 g, is set aside and processed separately in Example 4.1.

Elemental analysis: (308.42)

|  | % C |  | % H |
|---|---|---|---|
| calculated: | 81.78 | calculated: | 7.84 |
| found: | 81.84 | found: | 7.98 |

3.2) Enol Chlorination of p,p-Diketone, bis[4-(2-methyl-propionyl)-phenyl]-methane 60.0 g (0.1945 mol) of recrystallized bis[4-(2-methyl-propionyl)-phenyl]-methane with 2.7% [3-(2-methyl-propionyl)-phenyl-[4-(2-methyl-propionyl)-phenyl]-methane from the Friedel-Crafts reaction are dissolved in 150 ml of chlorobenzene and heated to 55–60° C. by means of an oil bath. The chlorination is carried out analogously to Example 1.2. There are obtained 73.8 g of a yellowish liquid, which begins to crystallise. The product is recrystallised from 75 g of hexane and then from 65 g of methanol, filtered and dried. There are obtained 30.6 g of white crystals, which melt at 70.4–73.1° C. 99% p,p-isomer and about 1% m,p-isomer are now found in the ¹H-NMR spectrum.

Elemental analysis: (377.31)

|  | % C |  | % H |  | % Cl |
|---|---|---|---|---|---|
| calculated: | 66.85 | calculated: | 5.88 | calculated: | 18.79 |
| found: | 66.94 | found: | 6.02 | found: | 19.20 |

3.3a) Hydrolysis of p,p-dichloro Compound, bis[4-(2-chloro-2-methyl-propionyl)-phenyl]-methane 25.0 g (0.066 mol) of bis[4-(2-chloro-2-methyl-propionyl)-phenyl]-methane from the chlorination reaction, dissolved in 30 g of toluene and 10 g of methanol, are hydrolysed analogously to Example 1, Variant 1.3a. After separation of the organic phase, the warm organic phase (about 50° C.) is diluted with solvent (30 ml of toluene), and about 3 g of water are then added thereto. The solution begins to crystallise spontaneously at about 30° C. After working up analogously to Example 1, Variant 1.3b, 19.2 g of white, granular crystals containing water of crystallisation are obtained. This corresponds to a yield of 80.8% of theory (358.44) of bis[4-(2-hydroxy-2-methyl-propionyl)-phenyl]-methane. >99% para-para Isomer and <1% meta-para Isomer are then found in the $^1$H-NMR spectrum. The crystals melt at 77.9–78.7° C. and contain 4.82% by weight water according to Karl Fischer water determination.

3.3b) Water-Free, Isomer-Free bis[4-(2-hydroxy-2-methyl-propionyl)-phenyl]-methane 5 g of the crystals containing water of crystallisation (Example 3.3a) are dissolved in 50 ml of toluene and heated to 60° C. 5 g of anhydrous calcium chloride are then added, and stirring is carried out for two hours. The suspension is filtered and the filtrate is concentrated in a vacuum rotary evaporator to about 20 ml. The product begins to crystallise at room temperature overnight. The crystals are washed with a small amount of toluene and dried in vacuo. 2.8 g of white crystals are obtained. >99.5% para-para isomer and <0.5% meta-para isomer are then found in the $^1$H-NMR spectrum. The crystals melt at 91.3–92.0° C. and contain <0.1% by weight water according to Karl Fischer water determination.

Elemental analysis: (340.42)

|  | % C |  | % H |
|---|---|---|---|
| calculated: | 74.09 | calculated: | 7.11 |
| found: | 73.71 | found: | 7.11 |

3.3c) Recrystallisation of the Isomer-free Hydrolysis Product 50 g of isomer-free bis[4-(2-hydroxy-2-methyl-propionyl)-phenyl]-methane containing water of crystallisation are heated to 70° C. in 75 g of toluene in order to dissolve the product. At 68° C., all the material has dissolved. A further 7.8 g of water are added. The temperature is controlled by means of an oil bath. At 50° C., the first crystals begin to form spontaneously. When crystallisation is complete, the suspension is filtered over a suction filter and washed with 62.5 g of cold toluene. The 55.4 g of white crystals are dried in vacuo to constant weight. 44.7 g of white, granular, compact crystals containing water of crystallisation are obtained. The crystals of the isomer-free product melt at 81.8–84.3° C. and contain 5.10% by weight water according to Karl Fischer water determination. FIG. 4 shows the X-ray powder spectrum with the characteristic lines at a 2-theta angle of 6.67; 9.65; 14.00; 14.85; 15.15; 15.47; 15.95; 16.41; 17.69; 19.81; 20.21; 21.39; 22.17; 22.61; 23.39; 25.91; 27.13; 27.91; 28.67.

The mother liquor is concentrated in vacuo. There are obtained 1.1 g of yellowish oil, which crystallises.

Elemental analysis of the end sample: (358.44)

|  | % C |  | % H |
|---|---|---|---|
| calculated: | 70.37 | calculated: | 7.31 |
| found: | 70.05 | found: | 7.29 |

EXAMPLE 4

Preparation of [3-(2-hydroxy-2-methyl-propionyl)-phenyl]-[4-(2-hydroxy-2-methyl-propionyl)-phenyl]-methane, Compound of Formula I 4.1) Friedel-Crafts Reaction and Separation 168.2 g (1.0 mol) of diphenylmethane, 245.1 g (2.3 mol) of isobutyric acid chloride and 150 ml of 1,2-dichlorobenzene are combined and cooled to 5–0° C. by means of an ice bath. The acylation is carried out in Example 3.1.

After working up, the organic phase is concentrated in Example 3.1 and crystallised from hexane. The crystals, bis[4-(2-methyl-propionyl)-phenyl]-methane, are recrystallised from hexane again and chlorinated in Example 3.2. The filtrate, about 350 g, is processed separately in Example 4.1.

The filtrate from Example 3.1 is concentrated in a vacuum rotary evaporator and then combined with other suitable dichlorobenzene solutions from the Friedel-Crafts reaction. 100 g of water are added to the yellow solution, and the mixture is freed of the solvent, 1,2-dichlorobenzene, by means of steam distillation. The head temperature In the distillation is about 95° C. and the distillation lasts about 4 hours. About 155 ml of 1,2-dichlorobenzene are recovered. The residue is separated from the water. 170.4 g of yellowish oil are obtained. 58 g of hexane are added, and dissolution is carried out while hot. The solution is cooled, to room temperature, and then cooled further by means of an ice-bath. White crystals are formed. They are filtered off and washed with about 150 g of hexane. The mother liquor is concentrated in a vacuum rotary evaporator. 80 g of yellow-reddish oil are obtained, which shows about 24% m,p-isomer in the $^1$H-NMR spectrum. A further 20 g of hexane are added to the oil, and the mixture is placed in a refrigerator for the purposes of crystallisation. The liquid is decanted off and concentrated in a vacuum rotary evaporator. 45 g of yellow-reddish oil are obtained, which shows about 37% m,p-isomer in the $^1$H-NMR spectrum. The various crystalline portions are dried and used for the preparation of pure p,p-isomer.

The liquid portion of 45 g is separated in portions over a preparative HPLC column from Varian. Since the separation is incomplete, only the first fractions are collected at the top and the rear fractions are fed back again because they contain too much p,p-isomer. After many passes through the column, there are obtained from the front fractions 1.9 g of meta-para isomer, [3-(2-methyl-propionyl)-phenyl]-[4-(2-methyl-propionyl)-phenyl]-methane, which in the GC and $^1$H-NMR, contains about 94% m,p-isomer and still contains about 3% m,m-isomer and about 3% p,p-isomer. The 1.9 g of yellowish oil collected are brominated without being purified further.

4.2) Enol Bromination of m,p-Diketone, [3-(2-methyl-propionyl)-phenyl]-[4-(2-methyl-propionyl)-phenyl]-methane 1.96 g (6.16 mmol) of separated [3-(2-methyl-propionyl)-phenyl]-[4-(2-methyl-propionyl)-phenyl]-methane are dissolved in 20 ml of chlorobenzene, and one drop of chlorosulfonic acid is added thereto. 1.97 g (12.32 mmol) of bromine are then dissolved in 50 ml of chlorobenzene and added dropwise at room temperature in a period of about 3 hours. The conversion is checked with a $^1$H-NMR spectrum. The slightly yellowish solution is concentrated in a rotary evaporator. 2.9 g of yellow oil, [3-(2-bromo-2-methyl-propionyl)-phenyl]-[4-(2-bromo-2-methyl-propionyl)-phenyl]-methane, are obtained.

4.3) Hydrolysis of m,p-dibromo Compound, [3-(2-bromo-2-methyl-propionyl)-phenyl]-[4-(2-bromo-2-methyl-propionyl)-phenyl]-methane 2.0 g (15 mmol) of NaOH concentrated to 30%, 20 ml of deionised water and 20 ml of methanol are combined and heated to 50° C. by means of an oil bath. 2.9 g (6.16 mmol) of [3-(2-bromo-2-methyl-propionyl)-phenyl]-[4-(2-bromo-2-methyl-propionyl)-phenyl]-methane, dissolved In 20 ml of toluene and 10 ml of methanol, are then added dropwise, with thorough stirring, in a period of about one hour. The alkaline mixture (about pH 12) is then stirred for about three hours at 55–60° C. The conversion is checked with a $^1$H-NMR sample. The mixture is then adjusted dropwise to a pH of about 1–2 with about 1.0 g of 16% hydrochloric acid and stirred at 50° C. for one hour in order to complete the reaction. The conversion is checked with a $^1$H-NMR sample. When the hydrolysis is complete, the reaction mixture is neutralised with a small amount of dilute sodium hydroxide solution. The two phases are separated in a separating funnel. The organic phase is concentrated in a rotary evaporator. 2.8 g of brownish oil are obtained (Example 4.3). It is dissolved in 20 ml of toluene and washed with 10 ml of water. The toluene solution is concentrated in a rotary evaporator and dried under a high vacuum. 2.0 g of yellowish oil are obtained. About 94% m,p-isomer, about 3% m,m-isomer and about 3% p,p-isomer, determined by evaluation of the integrals of the aromatic protons, are found in the $^1$H-NMR spectrum. No water-containing crystals have formed from the liquid m,p-isomer.

A sample of the mother liquor from Example 1d.5 is purified by flash chromatography over silica gel 60 (0.040–0.063 mm) from Merck. A mixture of ethyl acetate: hexane mixture 1:2 is used as eluant. Very surprisingly, the largest amount of the meta-para isomer is to be found in the mother liquor and not in the crystals. About 36% para-para isomer and about 64% meta-para isomer, determined by evaluation of the integrals of the aromatic protons, are found in the $^1$H-NMR spectrum (Example 1d.5a). The proportion of meta-para compound in the crystals has fallen to about 1–2%. That value is estimated from the difference with respect to the value in the mother liquor. In the $^1$H-NMR spectrum of the crystals, such a low value can only be estimated roughly. An improved method of determining the distribution of isomers after crystallisation is described in Example 1e.

The proportion of meta-para compound in the chromatographed mother liquors is between 60 and 80%, in the case of previous crystallisation of the crude product with water and toluene as solvent. The proportion of meta-para compound in the crystals has in most cases fallen to about 1–3%. Those values are calculated from the differences relative to the values in the mother liquors. In the $^1$H-NMR spectrum of the crystals, such low values can only be estimated roughly.

Comparison Tests

EXAMPLE 5 FOR COMPARISON

Hydrolysis Analogous to Example 1.3a and Working up Analogous to Method E (Epoxy Ether Hydrolysis) as Described in EPA 003 002

Working up Without Addition of Water 139.13 g (1.043 mol) of NaOH concentrated to 30% and 139 ml of deionised water and 137.6 g of methanol are combined. The temperature rises to about 35° C. The mixture is then heated to 50° C. by means of an oil bath. There are then added dropwise in a period of about one hour, with thorough stirring, 319.6 g (0.4348 mol) of a solution, in 1,2-dichlorobenzene, of the isomeric mixture of bis[4-(2-chloro-2-methyl-propionyl)-phenyl]-methane with [3-(2-chloro-2-methyl-propionyl)-phenyl]-[4-(2-chloro-2-methyl-propionyl)-phenyl]-methane from the chlorination reaction Example 1.2, additionally diluted with 68.7 g of methanol. The internal temperature slowly rises to 55–60° C. The alkaline mixture (about pH 11) is then stirred for about four hours at 55–60° C. The conversion is checked with a GC sample and a $^1$H-NMR sample. The mixture is then cooled to 45° C. and adjusted dropwise to a pH of about 1–2 with about 32 g of 16% hydrochloric acid. The colour of the emulsion changes from a strong yellow to yellow and the temperature rises to 53° C. The mixture is then stirred for about 2–3 hours. The conversion is checked with a $^1$H-NMR sample. When the hydrolysis is complete, the reaction mixture is neutralised with a small amount of dilute sodium hydroxide solution (5.5 g). The two phases are separated at about 50° C. in a separating funnel. 200 ml of water are added to the clear organic phase, which Is then stirred at 60° C. and separated off again. The phase separation is slow the second time. The cloudy, warm organic phase is diluted with toluene and then concentrated at 60° C. in a vacuum rotary evaporator in order to remove residual methanol and water. There are obtained 246.2 g of yellow-reddish solution of the end product, an isomeric mixture with bis[4-(2-hydroxy-2-methyl-propionyl)-phenyl]-methane as the main product, dissolved in 1,2-dichlorobenzene.

A small sample does not crystallise out in a test tube, even when seeded with water-free crystals.

A further small sample, which is left to stand in air for two days, slowly crystallises out under the influence of atmospheric moisture. The crystals melt at 57.9–59.4° C.

By contrast, a third small sample, to which a drop of water and a water-containing seed crystal are added, crystallises immediately.

The solution of the end product is then concentrated in a vacuum rotary evaporator at about 60° C. and at about 1 mbar, in order to remove the 1,2-dichlorobenzene. 149.7 g of yellow-reddish viscous oil are obtained. This corresponds to a yield of 101.1% of theory (340.42) over all three reaction steps. Two secondary components are still visible in the TLC. The $^1$H-NMR spectrum contains, in addition to the isomeric mixture, also a small amount of the ketal product. The water content of the crude product is 0.14% by weight in a Karl Fischer water determination. The oil (Example 5a) still smells a little of 1,2-dichlorobenzene.

A small sample of the concentrated oil does not crystallise out in a test tube, even when seeded with water-free crystals. Even dilution with diethyl ether does not result in crystallisation.

12.1 g of the concentrated oil are dissolved in 12.0 g of ethyl acetate and introduced onto a chromatography column and separated over about 0.5 kg of silica gel (silica gel 60 (0.040–0.063 mm) 230–400 mesh ASTM from Merck) with a hexane-ethyl acetate mixture (3:1). The fractions are collected and concentrated in a vacuum rotary evaporator. According to TLC, the product, a thick yellowish oil, is to be found in fractions 33–38 (4.2 g) and 39–53 (6.3 g).

The first fraction is pure isomeric mixture (TLC, $^1$H-NMR spectrum).

About 87.5% p,p-isomer and about 12.5% m,p-isomer are found in the $^1$H-NMR spectrum. The second fraction still has a small secondary component in the TLC. According to $^1$H-NMR spectrum it is the ketal product. The first fraction (Example 5b) begins to crystallise slowly after some days, more specifically from the top down. However, it does not crystallise through. The water content of the chromatographed product is 0.21% by weight in a Karl Fischer water determination. The second fraction remains viscous. Its water content in a Karl Fischer water determination is 0.30% by weight.

EXAMPLE 6 FOR COMPARISON

Preparation of the Epoxy Ether Intermediate and Hydrolysis of the Epoxy Ether Intermediate Analogous to Methods D and E (Epoxy Ether Hydrolysis) as Described in EPA 003 002

Working up Without Addition of Water

Preliminary note: The chlorination of the diketone was carried out analogously to Method A for the halogenation. At the end, the solvent 1,2-dichlorobenzene is distilled off in vacuo at 1 mbar. The crude product begins to crystallise out overnight. It is used for the epoxy ether synthesis without being purified further.

Method D of EPA 003 002: Preparation of the Epoxy Ether Intermediate:

73.6 g t.q. (0.177 mol t.q.) of the isomeric mixture of bis[4-(2-chloro-2-methyl-propionyl)-phenyl]-methane with [3-(2-chloro-2-methyl-propionyl)-phenyl]-[4-(2-chloro-2-methyl-propionyl)-phenyl]-methane from the chlorination reaction are dissolved in 80 ml of methanol puriss. and heated. At 45° C. and above, 80.0 g (0.444 mol) of 30% sodium methoxide solution in methanol are added dropwise. The temperature slowly rises to 60° C. and sodium chloride precipitates out. Duration of the dropwise addition is about 30 minutes. The conversion is checked with a GC. The methanol is then distilled off in a vacuum rotary evaporator. 100 ml of diethyl ether and 100 ml of water are added to the viscous residue, 98.4 g, and extraction is carried out. The ether phase is separated off, washed with 10 ml of water and then dried over Na$_2$SO$_4$ and concentrated. There are obtained 68.75 g t.q. of a viscous brown oil, which is checked with a $^1$H-NMR sample. The product, the epoxy ether intermediate, is hydrolysed in the next step according to Method E without being purified further.

Method E of EPA 003 002: Hydrolysis of the Epoxy Ether Intermediate:

200 ml of water are added to 68.75 g t.q. (0.177 mol t.q.) of the isomeric mixture of bis[4-(2-methoxy-3,3-dimethyl-oxiran-2-yl)-phenyl]-methane with 2-methoxy-3,3-dimethyl-2-[4-(3-(2-methoxy-3,3-dimethyl-oxiran-2-yl)-phenyl]methyl-phenyl]-oxirane from the epoxy ether stage, and the mixture is heated to 70° C. 1.3 g of 16% hydrochloric acid solution are then added dropwise until a pH of about 1 is reached. The temperature slowly rises to 83° C. Further heating is carried out to reflux at about 87° C. The conversion is checked with a $^1$H-NMR sample. After one hour's reflux, the two-phase orange reaction mixture is neutralised with 1.7 g of 15% sodium hydroxide solution and separated in a separating funnel while warm. There are obtained 64.8 g t.q. of a viscous reddish oil, which is dissolved with 150 ml of diethyl ether. The ether solution is dried over Na$_2$SO$_4$ and concentrated. 65.4 g t.q. of viscous reddish oil are obtained (Example 6a). This corresponds to a crude yield of 102% of theory. A secondary component is still visible in the TLC. In the $^1$H-NMR spectrum, a small amount of the ketal product is still to be found in addition to the isomeric mixture. The water content of the crude product is <0.3% in a Karl Fischer water determination.

15.0 g of the crude product are purified by means of flash chromatography over silica gel 60 (0.040–0.063 mm) from Merck. A mixture of ethyl acetate:hexane mixture 1:3 is used as eluant. 10.9 g of pure product are isolated as the main fraction (Example 15b). This corresponds to a yield of 74.1% of theory. It is pure isomeric mixture, a viscous yellowish oil, which does not crystallise. About 87% p,p-isomer and about 13% m,p-isomer are found in the $^1$H-NMR spectrum. The water content of the chromatographed product is 0.31% by weight in a Karl Fischer water determination. In the next fraction, 0.4 g of oil, the product still contains a secondary product, which is recognised by means of a $^1$H-NMR sample as the ketal product.

EXAMPLE 7 FOR COMPARISON

Hydrolysis and Working up Analogous to Method F (Epoxy Ether Hydrolysis) as Described in EPA 003 002

Batch: 0.238 mol

Preliminary note: Chlorination of the diketone was carried out analogously to Method A of EP 003 002. Finally, the solvent 1,2-dichlorobenzene is distilled off in vacuo at 1 mbar. The crude product begins to crystallise out overnight. After recrystallisation from ethanol, it is used for the hydrolysis according to Method F. M.p.: 69.4–71.0° C.

Method F of EPA 003 002: Hydrolysis of the Dichloro Compound:

90.0 g t.q. (0.238 mol) of crystals of the isomeric mixture of bis[4-(2-chloro-2-methyl-propionyl)-phenyl]-methane with [3-(2-chloro-2-methyl-propionyl)-phenyl]-[4-(2-chloro-2-methyl-propionyl)-phenyl]-methane from the chlorination reaction are heated at reflux with 229.1 g (0.572 mol) of 10% sodium hydroxide solution. At about 70° C., the dichloro compound melts and, when stirred, yields an emulsion. At 94° C., gentle reflux begins. After 25 minutes, about 3.9% starting material have been converted, after 2 hours about 7.6% and after 4 hours about 14% starting material (estimate from the $^1$H-NMR spectrum). Only starting material, mono compound and product are to be found in the thin-layer chromatogram. In order to accelerate the hydrolysis, the mixture is cooled to 60° C. and then 100 g of methanol are added as solvent and the mixture is heated to reflux (about 60° C.). After 30 minutes, about 80% starting material (estimate from the $^1$H-NMR spectrum) have been converted, and after 90 minutes all the starting material has been converted. The emulsion is diluted at 62° C. with 100 g of toluene and cooled to 43° C. When 21.8 g of 16% hydrochloric acid solution are added in order to achieve a pH of 1–2, the temperature rises to 49° C. The emulsion is heated to reflux again (about 60° C.) and then stirred for 2 hours until all the ketal (monitoring with the $^1$H-NMR spectrum) has been hydrolysed. The emulsion is then adjusted to pH 7 with 1.2 g of 15% sodium hydroxide solution. The aqueous phase is separated off in a separating funnel and extracted with 20 g of toluene. The organic phase is washed with 20 g of water and then combined with the toluene used for washing. The organic phase is then concentrated in a vacuum rotary evaporator. 82.3 g of yellow oil are obtained. This is dissolved again in 200 g of toluene and then dried over $Na_2SO_4$ and concentrated in a vacuum rotary evaporator. There are obtained 81.3 g of viscous yellow oil, which does not crystallise. This corresponds to a t.q. yield of 100.3% of theory (340.42). It is an isomeric mixture (Example 7a) with bis[4-(2-hydroxy-2-methyl-propionyl)-phenyl]-methane as the main component. The structure is confirmed with a $^1$H-NMR sample. The composition in the isomeric mixture has shifted markedly in favour of the p,p-isomer. This was caused by the recrystallisation of the dichloro compound. The water content of the crude product is 0.30% by weight in a Karl Fischer water determination. After standing for a relatively long period of time, the crude product solidifies. The crystals melt at 87.1–89.0° C.

19.09 of the crude product are purified by means of flash chromatography over silica gel 60 (0.040–0.063 mm) from Merck. A mixture of ethyl acetate:hexane mixture 1:3 is used as eluant. 10.5 g of pure product (Example 7b) are isolated as the main fraction. This corresponds to a yield of 55.4% of theory. It is a viscous yellowish oil which initially does not crystallise. In the $^1$H-NMR spectrum, only traces of the m,p-isomer are found in addition to the p,p-isomer. The water content of the chromatographed product is 0.50% by weight in a Karl Fischer water determination. In the next fraction, 7.0 g of oil, the product still contains a small amount of a secondary product, which is recognised as a ketal product by means of a $^1$H-NMR sample.

After standing for a relatively long period of time, the oil crystallises. The crystals melt at 89.6–91.6° C. FIG. 5 shows the X-ray powder spectrum with the characteristic lines at a 2-theta angle of 10.77; 11.27; 16.49; 17.27; 17.89; 21.57; 22.63; 26.05; 28.75.

EXAMPLE 8

Example for Determining the Hygroscopicity

It was observed on various occasions in the case of the water-free products that they are hygroscopic at room temperature and crystallise, or change crystal form, under the effect of moist air. In order to check this, samples of water-free products, products containing isomers as well as isomerically pure products, are placed into small Petri dishes, in the form of an oil or in the form of a solidified mass, and then spread flat. The Petri dishes are stored at room temperature in a desiccator, which contains a dish of water.

Samples from the following Examples are weighed out:
Example 1.3c
Example 2
Example 3.3c
Example 5a
Example 6a
Example 7a As the days pass, the habit of the samples changes and they all crystallise. After two weeks, samples are removed and the water content is determined according to Karl Fischer. In all samples, it is now between 3.9 and 4.8% with a theoretical content of 5.03% for one water of crystallisation per molecule. After one month, the resulting crystals are pulverised in an agate mortar and submitted for the recording of an X-ray powder spectrum. At the same time, the water content is determined according to Karl Fischer. In all samples it is now between 4.6 and 5.1% with a theoretical content of 5.03% for one water of crystallisation per molecule. All the X-ray powder spectra of the samples are now typical of water-containing crystals. FIGS. 6 to 11 show the X-ray powder spectra of the samples with the characteristic lines at a 2-theta angle of 6.70; 9.70; 14.00; 14.90; 15.19; 15.59; 15.99; 16.43; 17.67; 19.85; 20.27; 21.45; 22.25; 26.00; 28.83.

For comparison, three further samples are submitted for the recording of an X-ray powder spectrum. (FIGS. 12 to 14) A common feature of all these samples is that they have a markedly lower water content, from 2.0 to 3.9%, than the usual water-containing samples. They are produced by the subsequent forced removal of water of crystallisation, for example by distillation or after-drying of water-containing crystals under a high vacuum. A common feature of all three samples is that they now simultaneously have the characteristic lines for water-containing and water-free crystals. These are the samples Example 1.3c, Example 1.3a and Example 3.3c after-dried under HV. The forced after-drying in a vacuum rotary evaporator has the particularly unexpected effect that the crystals cake together to form non-dusty loose spherules which are readily pourable.

Using the product bis[4-(2-methyl-propionyl)-phenyl]-methane and the isomeric mixture, it is also possible to prepare crystals with methanol instead of with water. Unfortunately, the methanol slowly evaporates on drying or when left to stand in the air. The crystals are too unstable.

Notes Relating to the Examples

The water-containing crystals from the various Examples are unstable above 50° C. and begin slowly to lose water. Because of this phenomenon, the melting point determinations are subject to systematic error and become inaccurate. Depending on the rate of heating, differing results are obtained. Furthermore, the water-containing crystals can become reorganised during storage and have a higher melting range after some weeks.

On drying of the water-containing crystals under a very good vacuum, a portion of the water of crystallisation is lost. If drying is carried out at higher temperatures, the water-containing crystals can begin to sinter.

The water-free crystals tend to be amorphous and crystallise with difficulty. However, they melt at a markedly higher temperature. They are highly soluble in organic solvents. The water-containing crystals are less readily soluble in organic solvents and can therefore be isolated more readily from crude products.

The water-free crystals are markedly hygroscopic at room temperature. When they are stored in a desiccator over a dish of water, they absorb most of the possible water within days or weeks. In so doing, the crystals change in appearance and become powdery.

The X-ray powder spectra of water-containing and water-free crystals differ greatly. However, the differences in the X-ray powder spectra between the isomerically pure crystals and the isomeric mixtures from the Examples are slight. The crystals crystallise with the same unit cell in each case.

APPLICATION EXAMPLES

Example A1

Overprint Coating Formulation (with Aminoacrylate)

| Component | % by wt. |
|---|---|
| Ebecryl 605 | 30.0 |
| Ebecryl 7100 | 10.0 |
| Ebecryl 40 | 5.0 |
| OTA 480 | 30.0 |
| TPGDA | 24.0 |
| Ebecryl 1360 | 0.5 |
| Dow Corning 57 | 0.5 |
| Σ | 100.0 |

OTA 480: a glycerol propoxylate triacrylate (UCB)
TPGDA: tripropylene glycol diacrylate
Ebecryl 605: bisphenol A epoxy acrylate, diluted with 25% TPGDA (UCB)
Ebecryl 7100: aminoacrylate (UCB)
Ebecryl 40: pentaerythritol ethoxylate tetraacrylate (UCB)
Ebecryl 1360 silicone acrylate
Dow Corning 57: silicone additive, flow improver In each case 0.6 g of photoinitiator was weighed in per 10 g of formulation.
UV exposure device (IST): Two 120 W/cm medium-pressure mercury lamps, variable-speed conveyor belt
Curing rate: Determination of the stability against wiping of the cured clear coats; figure given in terms of m/min conveyor belt speed of the UV exposure device; applied layer thickness 6 μm (Erichson knife device) on cardboard
Yellowing/gloss: Measurement of the b* value 15 min after curing (curing at a conveyor belt speed of the UV exposure device of 10 m/min); applied layer thickness 100 μm (manual knife) on white-coated chipboard. The measuring angle for the gloss measurement is 20°.
Odour rating: Curing of the clear coats at a predetermined curing rate, applied layer thickness 6 μm on aluminium foil. Rating: 0=odourless, 1=very slight, 2=slight, 3=marked, 4=pronounced, 5=very pronounced. Inherent odour of the substrate: 1.
The following Tables show the results:

a) Comparison Between Water-Containing Product Para-Para Compound) and Darocur 1173, Irgacure 184, Irgacure 500, Irgacure 2959, Esacure KIP 150 and Esacure KIP 100 F

| Photoinitiator Example | Curing rate [m/min] | b* | Gloss [%] | Odour rating |
|---|---|---|---|---|
| 3.3a | 190 | 8.5 | 91 | 3 |
| Darocur 1173 | 70 | 7.8 | 87 | 5 |
| Irgacure 184 | 60 | 7.3 | 89 | 5 |
| Irgacure 2959 | 60 | 7.8 | 89 | 3 |
| Esacure KIP 150 | 90 | 7.1 | 88 | 3 |
| Esacure KIP 100 F | 80 | 7.6 | 89 | 3 |

Darocur 1173: 2-hydroxy-2-methyl-1-phenylpropan-1-one (Ciba)
Irgacure 184: (1-hydroxy-cyclohexyl)phenyl ketone (Ciba)
Irgacure 2959: 1-[4-(2-hydroxyethoxy)-phenyl]-2-hydroxy-2-methyl-1-propan-1-one (Ciba)
Esacure KIP 150: oligo-[2-hydroxy-2-methyl-1-[4-(1-methylvinyl)phenyl] propanone], (Lamberti)
Esacure KIP 100F: oligo-[2-hydroxy-2-methyl-1-[4-(1-methylvinyl)-phenyl]-propanone + 2-hydroxy-2-methyl-1-phenylpropan-1-one b) Comparison Between Water-Containing Product and Water-Free Product According to EP 003 002

| Photoinitiator Example | Curing rate [m/min] | b* | Gloss [%] | Odour rating |
|---|---|---|---|---|
| 1.3a | 180 | 9.0 | 88 | 2.5 |
| 2 | 180 | 9.2 | 88 | 2.5 |
| 5a | 160 | 10.9 | 88 | 3 |
| 5b | 170 | 9.5 | 88 | 2 |
| 7a | 180 | 8.9 | 88 | 2.5 |
| 7b | 180 | 9.1 | 88 | 2.5 | c) Comparison Between Water-Containing Low-Melting Product and Water-Containing High-Melting Product

| Photoinitiator Example | Curing rate [m/min] | b* | Gloss [%] | Odour rating |
|---|---|---|---|---|
| 1.3a 68–70° C. | 170 | 9.3 | 88 | 2.5 |
| 1.3b 71–74° C. | 180 | 9.5 | 88 | 2.5 |
| 1.3c 87–90° C. | 180 | 8.8 | 88 | 2.5 | d) Comparison Between Water-Containing Product of Isomeric Mixture, Water-Containing Product of Pure Para-Para Compound and Water-Free Product of Pure Meta-Para Compound

| Photoinitiator Example | Curing rate [m/min] | b* | Gloss [%] | Odour rating |
|---|---|---|---|---|
| 1.3a | 180 | 9.0 | 88 | 2.5 |
| 3.3c | 190 | 9.2 | 88 | 2.5 |
| 4.3 | 150 | 7.8 | 85 | 2.5 | e) Comparison Between Water-Free Product of Isomeric Mixture and Water-Free Product of Pure Para-Para Compound

| Photoinitiator Example | Curing rate [m/min] | b* | Gloss [%] | Odour rating |
|---|---|---|---|---|
| 2 | 180 | 9.2 | 88 | 2.5 |
| 3.3b | 180 | 9.3 | 88 | 2.5 |
| 5b | 170 | 9.5 | 88 | 2 | f) Comparison Between Water-Containing Product of Isomeric Mixture with Known Meta-Para Content, Water-Free Product of Isomeric Mixture from the Chromatographed Mother Liquor, and Water-Free Product of Pure Meta-Para Compound

| Photoinitiator Example | Curing rate [m/min] | b* | Gloss [%] | Odour rating |
|---|---|---|---|---|
| 1.e 1% m-p | 180 | 6.8 | 88 | 2 |
| 1.f 12% m-p | 180 | 8.5 | 88 | 2 |

| Photoinitiator Example | Curing rate [m/min] | b* | Gloss [%] | Odour rating |
|---|---|---|---|---|
| 1.fa 4% m-p | 180 | 7.5 | 87 | 2 |
| 1.fb 7% m-p | 170 | 7.0 | 86 | 2.5 |
| 1d.5a 64% m-p | 170 | 9.0 | 85 | 2.5 |
| 4.3 100% m-p | 150 | 7.8 | 85 | 2.5 |

Example A2

Overprint Coating Formulation (Without Aminoacrylate)

| Component | % by wt. |
|---|---|
| Ebecryl 605 | 35.0 |
| Ebecryl 40 | 10.0 |
| OTA 480 | 30.0 |
| TPGDA | 24.0 |
| Ebecryl 1360 | 0.5 |
| Dow Corning 57 | 0.5 |
| Σ | 100.0 |

OTA 480: a glycerol propoxylate triacrylate (UCB)
TPGDA: tripropylene glycol diacrylate
Ebecryl 605: bisphenol A epoxy acrylate, diluted with 25% TPGDA (UCB)
Ebecryl 40: pentaerythritol ethoxylate tetraacrylate (UCB)
Ebecryl 1360 silicone acrylate
Dow Corning 57: silicone additive, flow improver In each case 0.6 g (or 0.8 g) of photoinitiator was weighed in per 10 g of formulation.
UV exposure device (IST): Two 120 W/cm medium-pressure mercury lamps, variable-speed conveyor belt
Curing rate: Determination of the stability against wiping of the cured clear coats; figure given in terms of m/min conveyor belt speed of the UV exposure device; applied layer thickness 6 μm (Erichson knife device) on cardboard
Yellowing/gloss: Measurement of the b* value 15 min after curing (curing at a conveyor belt speed of the UV exposure device of 10 m/min); applied layer thickness 100 μm (manual knife) on white-coated chipboard. The measuring angle for the gloss measurement is 20°.
Odour rating: Curing of the clear coats at a predetermined curing rate, applied layer thickness 6 μm on aluminium foil. Rating: 0=odourless, 1=very slight, 2=slight, 3=marked, 4=pronounced, 5=very pronounced. Inherent odour of the substrate: 1.
The following Tables show the results:

a) Comparison Between Water-Containing Product (Pure Para-Para Compound) and Darocur 1173, Irgacure 184, Irgacure 500, Irgacure 2959, Esacure KIP 150 and Esacure KIP 100 F with 0.6 g of Photoinitiator

| Photoinitiator Example | Curing rate [m/min] | b* | Gloss [%] | Odour rating |
|---|---|---|---|---|
| 3.3a | 100 | 11.8 | 89 | 3 |
| Darocur 1173 | 30 | 7.2 | 86 | 4 |
| Irgacure 184 | 20 | 6.1 | 88 | 4 |
| Irgacure 2959 | 40 | 6.3 | 88 | 2 |
| Esacure KIP 150 | 60 | 8.3 | 89 | 3 |
| Esacure KIP 100 F | 40 | 7.0 | 89 | 3 |

Darocur 1173: 2-hydroxy-2-methyl-1-phenylpropan-1-one (Ciba)
Irgacure 184: (1-hydroxy-cyclohexyl)phenyl ketone (Ciba)
Irgacure 2959: 1-[4-(2-hydroxyethoxy)-phenyl]-2-hydroxy-2-methyl-1-propan-1-one (Ciba)
Esacure KIP 150: oligo-[2-hydroxy-2-methyl-1-[4-(1-methylvinyl)phenyl] propanone], (Lamberti)
Esacure KIP 100 F: oligo-[2-hydroxy-2-methyl-1-[4-(1-methylvinyl)-phenyl]-propanone + 2-hydroxy-2-methyl-1-phenylpropan-1-one b) Comparison Between Water-Containing Product (Pure Para-Para Compound) and Darocur 1173, Irgacure 184, Irgacure 500, Irgacure 2959, Esacure KIP 150 and Esacure KIP 100 F with 0.8 g of photoinitiator

| Photoinitiator Example | Curing rate [m/min] | b* | Gloss [%] | Odour rating |
|---|---|---|---|---|
| 3.3a | 200 | 10.8 | 91 | 3 |
| Darocur 1173 | 60 | 6.9 | 88 | 5 |
| Irgacure 184 | 60 | 6.7 | 89 | 5 |
| Irgacure 2959 | 60 | 6.5 | 88 | 2 |
| Esacure KIP 150 | 120 | 8.6 | 89 | 3 |
| Esacure KIP 100 F | 80 | 7.6 | 89 | 3 | c) Comparison Between Water-Containing Product and Water-Free Product According to EP 003 002

| Photoinitiator Example | Curing rate [m/min] | b* | Gloss [%] | Odour rating |
|---|---|---|---|---|
| 1.3a | 100 | 11.3 | 89 | 2.5 |
| 2 | 90 | 12.2 | 86 | 3 |
| 5a | 70 | 13.2 | 87 | 3.5 |
| 5b | 100 | 12.2 | 87 | 2.5 |
| 7a | 100 | 12.0 | 88 | 2.5 |
| 7b | 100 | 11.8 | 88 | 2.5 | d) Comparison Between Water-Containing Low-Melting Product and Water-Containing High-Melting Product with 0.6 g of Photoinitiator

| Photoinitiator Example | Curing rate [m/min] | b* | Gloss [%] | Odour rating |
|---|---|---|---|---|
| 1.3a 68–70° C. | 100 | 12.0 | 88 | 2.5 |
| 1.3b 71–74° C. | 90 | 11.8 | 88 | 2.5 |
| 1.3c 87–90° C. | 100 | 12.0 | 89 | 2.5 | e) Comparison Between Water-Containing Product of Isomeric Mixture, Water-Containing Product of Pure Para-Para Compound and Water-Free Product of Pure Meta-Para Compound with 0.6 g of Photoinitiator

| Photoinitiator Example | Curing rate [m/min] | b* | Gloss [%] | Odour rating |
|---|---|---|---|---|
| 1.3a | 100 | 12.0 | 88 | 2.5 |
| 3.3c | 100 | 11.8 | 87 | 3 |
| 4.3 | 60 | 8.0 | 85 | 2 | f) Comparison Between Water-Free Product of Isomeric Mixture and Water-Free Product of Pure Para-Para Compound with 0.6 g of Photoinitiator

| Photoinitiator Example | Curing rate [m/min] | b* | Gloss [%] | Odour rating |
|---|---|---|---|---|
| 2 | 90 | 12.2 | 86 | 3 |
| 3.3b | 100 | 12.0 | 88 | 3 |
| 5b | 100 | 12.2 | 87 | 2.5 | g) Comparison Between Water-Containing Product of Isomeric Mixture with Known Meta-Para Content, Water-Free Product of Isomeric Mixture from the Chromatographed Mother Liquor, and Water-Free Product of Pure Meta-Para Compound

| Photoinitiator Example | Curing rate [m/min] | b* | Gloss [%] | Odour rating |
|---|---|---|---|---|
| 1.e 1% m-p | 100 | 12.0 | 88 | 2 |
| 1.f 12% m-p | 100 | 13.0 | 88 | 2 |
| 1.fa 4% m-p | 90 | 12.8 | 87 | 2.5 |
| 1.fb 7% m-p | 90 | 12.8 | 86 | 2.5 |
| 1d.5a 64% m-p | 60 | 10.0 | 84 | 2.5 |
| 4.3 100% m-p | 60 | 8.0 | 85 | 2 |

Example A3

Powder Coating Formulation

| Component | % by weight |
|---|---|
| Uracross P3125 (unsaturated polyester resin from DSM) | 76.5 |
| Uracross P3307 (vinyl ether polyurethane resin from DSM) | 20 |
| Worlee add 902 (flow agent from Worlée Chemie) | 0.5 |
| Resiflow PV5 (flow agent from Worlée Chemie) | 1.0 |
| Photoinitiator | 2.0 |
| Σ | 100.0 |

Extruded at 70° C. (Prism TS 16 Twin Screw Extruder)

The clear powder coating is applied to white-coated chipboard and to glass. (Wagner turbo gun); layer thickness: 75+/−5 μm. The coated samples are melted under an IR lamp (2 min, 140° C.) and cured.

UV exposure device (IST):Hg- and Fe-doped lamps each of 240 W/cm, Variable-speed conveyor belt, (curing rate: 10, 20 or 40 m/min)

Test Method:

König pendulum hardness according to DIN 53157.

Measurement was carried out directly after curing (0 h) and after 24 h.

Methyl ethyl ketone blister test: The time until the coating begins to come away is measured.

Methyl ethyl ketone soak test, the loss in weight in % is measured.

| Photo-initiator | Curing rate m/min | Pendulum hardness (sec) | | MEK blister test (min) | | MEK soak test % | b* value |
|---|---|---|---|---|---|---|---|
| | | 0 h | 24 h | 0 h | 24 h | 0 h | 0 h |
| Irgacure 184 | 10 | 132 | 146 | 33 | 35 | 1.4 | 1.1 |
| | 20 | 125 | 137 | 28 | 28 | 0.2 | |
| | 40 | 115 | 126 | 14 | 14 | −0.7 | |
| Example 1.3a | 10 | 112 | 119 | 20 | 19 | 1.3 | 3.6 |
| | 20 | 109 | 132 | 14 | 16 | −3.7 | 1.7 |
| | 40 | 97 | 116 | 15 | 09 | −2.7 | 0.7 |

Example A4

Formulation for Blue Flexographic Printing Ink

| | |
|---|---|
| IRR 440 (acrylic oligomer in acrylate)s | 26.9 |
| OTA 480 | 19.0 |
| Ebecryl 645 (modified bisphenol A epoxy acrylate) | 18.0 |
| Hexanediol diacrylate | 13.0 |
| Ebecryl 220 (hexafunctional aromatic urethane acrylate (UCB)) | 10.0 |
| Ebecryl 168 (acidic methacrylate, adhesion agent) | 1.3 |
| Dow Corning 57[2] | 0.7 |
| Irgalite Blue GLO[3] | 11.1 |
| Σ | 100.0 |

UV exposure device (IST): One 120 W/cm medium-pressure mercury lamp, variable-speed conveyor belt Substrate: white PE film Application: test assembly, 1.38 g/m$^2$, corresponds to an optical density of 1.45

Properties tested: through-curing (TC), surface curing (SF)

Results of the Comparison Tests

| Product | Concentration [% by wt.] | TC [m/min] | SF [m/min] |
|---|---|---|---|
| Example 1.3a | 6 | 120 | 110 |
| Example 1.3a | 8 | 160 | 140 |
| IRGACURE 369[1] | 6 | 90 | 170 |
| IRGACURE 369[1] | 8 | 150 | 200 |
| IRGACURE 907[1] + QUANTACURE ITX[2] | 6 + 0.5 | 100 | 100 |

-continued

| Product | Concentration [% by wt.] | TC [m/min] | SF [m/min] |
|---|---|---|---|
| IRGACURE 1300[1] | 6 | 20 | 20 |
| IRGACURE 1300[1] | 8 | 70 | 100 |

Irgacure 369: 2-benzyl-2-dimethylamino-1-(4-morpholinophenyl)-butanone-1
IRGACURE 1300[1] (30% Irgacure 369 + 70% Irgacure 651) Irgacure 651: 2,2-dimethoxy-1,2-diphenylethan-1-one
[1]Ciba Specialty Chemicals
[2]Lambson

Example A5

Example of a Dispersion in Water

Preparation of an Aqueous Photoinitiator Formulation
40% photoinitiator of Example 1.3a
4% dispersant, sodium salt of a carboxylic acid copolymer, $^{RTM}$OROTAN 731 DP from Rohm+Haas Company;
0.1% bactericide, 1,2-benzisothiazol-3-one, $^{RTM}$PROXEL BD from Novartis AG;
55.9% water (deionised).

1.1 Preparation of the Suspension
In a glass beaker,

| | |
|---|---|
| 0.6 g | of bactericide ($^{RTM}$PROXEL BD) and |
| 26.0 g | of dispersant ($^{RTM}$OROTAN DP 731) are dissolved in |
| 363.4 g | of deionised water at room temperature. |
| 260.0 g | of photoinitiator are introduced into the resulting solution, and stirring is carried out for about one hour. |
| 650 g | of an aqueous suspension are obtained. |

1.2 Pre-grinding
At room temperature, the suspension obtained according to Example A51.1 is pre-ground three times in a cross-toothed colloid mill (stator-rotor principle, water-cooled; from Fryma AG Maschinenbau, Rheinfelden, Switzerland) by a repeating process with the narrowest grinding gap setting. The temperature of the suspension does not exceed 35° C. during the grinding. After the grinding operation, the largest particles have a diameter of about 100 micrometers.

1.3 Fine Grinding
An impeller-type ball mill (Bachofen KDL type with 0.6 litre grinding cylinder) Is filled with 80–83% by volume of glass beads having a diameter of 1 mm (=480–500 g of glass beads, based on the capacity of the grinding cylinder), and the water cooling of the mill is set in operation. At room temperature, the aqueous suspension pre-ground according to Example 1.2 is finely ground three times by a repeating process at a shaft speed of 2000 rev/min by means of the impeller-type ball mill. The throughput Is about 9 litres of suspension/hour. The temperature of the grinding stock is kept below 35° C. by jacket cooling. After the third grinding pass, the necessary fineness of particle size has been achieved. The particle size distribution in the suspension is determined using a laser granulometer. The 50% median value is about 2.5 micrometers; the largest particles have a diameter of about 12 micrometers. A homogeneous formulation that flows readily at room temperature is obtained; its storage stability at 20–25° C. is more than one month (i.e. no sedimentation and no phase separation occur).

Example A6

A clear Dual-Cure-System based on polyurethenes is prepared by mixing:

| | |
|---|---|
| 21.1 | Parts Desmophen ® LS 2009/1, hydroxy functional polyacrylate, (Bayer AG) |
| 32.3 | Parts Roskydal ® FWO 2518C, isocyanurate based urethane acrylate, 80% in butyl acetate (Bayer AG) |
| | Parts Baysilone ® OL 17, flow improver, 10% in Xylene (Bayer AG) |
| 0.3 | Parts Modaflow ®, flow improver (Monsanto) |
| 0.3 | Parts 1-Methoxy-2-propanol, (Fluka Chemicals) |
| 26.0 | Parts Byk ® 306, flow improver (Byk-Chemie) |
| 0.5 | Parts Roskydal ® FWO 2545 E, urethane acrylate with isocyanate groups |
| 11.2 | (Bayer AG) |

The samples were prepared by adding 3% of photoinitator as given in the table below.
The mixtures were applied to a white coil-coat aluminum, air-dried for 5 minutes at room temperature an heated on a hot plate at 120° C. for 10 minutes. Irradiation is the carried out using a Panacol F-450 Lamp with UVA emission. A tack free dry film with a thickness of approximately 40 μm is obtained.
45 Minutes after cure, the pendulum hardness according to König (DIN 53157) is measured.

| Initiator | pendulum hardness [sec] |
|---|---|
| 3% (Example 1.3a + Irgacure 819 819 (5:1)) 1.5% Tinuvin 400 + 1% Tinuvin 292 | 95 |

Irgacure 819 (Ciba) (Bis(2,4,6-trimethylbenzoyl)-phenylphosphineoxide)
Tinuvin 400 (Ciba) (a mixture of 2-[4-[(2-Hydroxy-3-dodecyloxypropyl)oxy]-2-hydroxyphenyl]-4,6-bis(2,4-dimethylphenyl)-1,3,5-triazine and 2-[4-[(2-Hydroxy-3-tridecyloxypropyl)oxy]-2-hydroxyphenyl]-4,6-bis(2,4-dimethylphenyl)-1,3,5-triazine)
Tinuvin 292(Ciba) ((1,2,2,6,6-pentamethyl-4-piperidinyl)sebacate)

Example A7

Curing of a UV-Curable Clear Lacquer as Wsed, for Example in the Automotive Industry.

A UV-curable clear lacquer is prepared by mixing the following components:

| | |
|---|---|
| 80.0 | parts of a hexafunktional urethane acrylate (Ebecryl 1290) |
| 20.0 | parts Butylacetate (Solvent) |

3% of the photoinitiator combination based on solids were well dissolved.
The Combination are 5 Parts from Example 1.3a combined with 1 part Irgacure 819. In addition 1.5% Tinuvin 400 And 1% Tinuvin 292 are added. The mixture is applied to a white cil coat aluminum panel and is cured using a Panacol F450 Lamp. The exposure time was 5 Min. A non-sticky cured film approximately 50 μm thick is obtained. 30 minutes after curing, the pendulum hardness according to König (DIN 53157) is determined in seconds. The higher the value, the greater is the hardness of the crosslinked surface.
The pendulum hardness measured is 147 s.

SUMMARY EXPLANATION OF THE FIGURES

FIGS. 1 and 2 show the X-ray powder spectra of water-containing isomeric mixtures of the compounds of formulae Ia and IIa.

FIG. 3 shows the X-ray powder spectrum of the water-free isomeric mixture of the compounds of formulae I and II.

FIG. 4 shows the X-ray powder spectrum of the water-containing pure para-para compound of formula IIa.

FIG. 5 shows the X-ray powder spectrum of the water-free pure para-para compound of formula II.

FIGS. 6 to 11 show the X-ray powder spectra of water-containing compounds, the water absorption having taken place owing to the hygroscopic properties of the water-free compounds, (Example 8)

FIGS. 6 to 7, 9 to 11 show the X-ray powder spectra of water-containing isomeric mixtures of the compounds of formulae Ia and IIa.

FIG. 8 shows the X-ray powder spectrum of the water-containing pure para-para compound of formula IIa.

FIGS. 12 to 14 show the X-ray powder spectra of water-containing isomeric mixtures of the compounds of formulae Ia and IIa with a smaller water content after removal of a portion of the water of crystallisation (Example 8).

The invention claimed is:

1. A crystalline isomeric mixture of α-hydroxy ketone compounds of formulae Ia and IIa

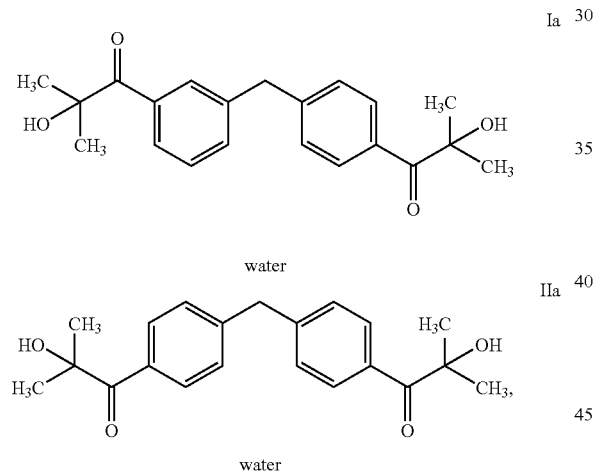

where the water content is from 2 to 8% by weight.

2. An isomeric mixture according to claim 1, having a content of para-para compound of from 99.9 to 25% by weight and having a content of meta-para compound of from 0.1 to 75% by weight.

3. A process for the preparation of a crystalline isomeric mixture of compounds of formulae Ia and IIa according to claim 1, which process comprises reacting diphenylmethane with isobutyric acid halide in the presence of a Friedel-Crafts catalyst, and chlorinating and hydrolysing the resulting isomeric mixture consisting of bis[4-(2-methyl-propionyl)-phenyl]-methane and [3-(2-methyl-propionyl)-phenyl]-[4-(2-methyl-propionyl)-phenyl] methane, hydrolysis of the isomeric mixture yielding an aqueous phase and an organic phase that comprises the hydrolysis product; wherein further processing of the hydrolysis product comprises the following steps
a) addition of from 3 to 20% by weight of water to the organic phase, crystallisation and isolation of the water containing isomeric mixture of formulae Ia and IIa and
b) where appropriate, drying of the isomeric mixture obtained in step a) to remove excess water and obtain a crystalline isomeric mixture.

4. A composition comprising
(A) at least one ethylenically unsaturated compound,
(B) an isomeric mixture of compounds of formulae Ia and IIa according to claim 1,
(C) optionally a film-forming binder based on a thermoplastic or thermocurable resin;
(D) optionally, further additives,
(E) optionally, further photoinitiators and coinitiators.

5. A process for the production of a scratch-resistant durable surface, wherein
(1) a composition according to claim 4 is prepared;
(2) the formulation is applied to a support; and
(3) curing of the formulation is carried out either only by means of irradiation with electromagnetic radiation having a wavelength of from 200 nm to within the IR range, or by irradiation with electromagnetic radiation and prior, simultaneous and/or subsequent action of heat.

6. A process according to claim 5 for the production of pigmented and non-pigmented surface coatings, overprint coatings, powder coatings, printing inks, gel coats, composite materials or glass fibre coatings.

7. A coated substrate which is coated on at least one surface with a cured composition according to claim 4.

8. A composition comprising
(A) an ethylenically unsaturated compound containing at least one aminoacrylate,
(B) an isomeric mixture of compounds of formulae Ia and IIa according to claim 1,
(C) optionally a film-forming binder based on a thermoplastic or thermocurable resin;
(D) optionally, further additives,
(E) optionally, further photoinitiators and coinitiators.

9. A process for the production of a scratch-resistant durable surface, wherein
(1) a composition according to claim 8 is prepared;
(2) the formulation is applied to a support; and
(3) curing of the formulation is carried out either only by means of irradiation with electromagnetic radiation having a wavelength of from 200 nm to within the IR range, or by irradiation with electromagnetic radiation and prior, simultaneous and/or subsequent action of heat.

10. A process according to claim 9 for the production of pigmented and non-pigmented surface coatings, overprint coatings, powder coatings, printing inks, gel coats, composite materials or glass fibre coatings.

11. A coated substrate which is coated on at least one surface with a cured composition according to claim 8.

* * * * *